(12) United States Patent  
Salmon et al.

(10) Patent No.: US 8,450,243 B2
(45) Date of Patent: May 28, 2013

(54) HERBICIDAL QUINOLINE AND 1,8-NAPHTHYRIDINE COMPOUNDS

(75) Inventors: Roger Salmon, Bracknell (GB); Glynn Mitchell, Bracknell (GB); James Alan Morris, Bracknell (GB)

(73) Assignee: Syngenta Limited, European Regional Centre, Guildford (GB)

( * ) Notice: Subject to any disclaimer, the term of this patent is extended or adjusted under 35 U.S.C. 154(b) by 0 days.

(21) Appl. No.: 13/263,248

(22) PCT Filed: Mar. 31, 2010

(86) PCT No.: PCT/GB2010/000638
§ 371 (c)(1),
(2), (4) Date: Dec. 28, 2011

(87) PCT Pub. No.: WO2010/116122
PCT Pub. Date: Oct. 14, 2010

(65) Prior Publication Data
US 2012/0094833 A1    Apr. 19, 2012

(30) Foreign Application Priority Data

Apr. 6, 2009 (GB) .................................. 0905963.5
Oct. 5, 2009 (GB) .................................. 0917407.9

(51) Int. Cl.
*A01N 25/32* (2006.01)
*A01N 43/42* (2006.01)
*A01N 43/90* (2006.01)
*A01P 13/00* (2006.01)
*C07D 215/227* (2006.01)
*C07D 471/04* (2006.01)

(52) U.S. Cl.
USPC ........... 504/103; 504/130; 504/246; 504/247; 546/123; 546/156

(58) Field of Classification Search
None
See application file for complete search history.

(56) References Cited

U.S. PATENT DOCUMENTS

2011/0021352 A1* 1/2011 Mitchell et al. ............... 504/103

FOREIGN PATENT DOCUMENTS

| WO | 9746530 | 12/1997 |
| WO | 2006024820 | 3/2006 |
| WO | 2006132947 | 12/2006 |
| WO | 2009115788 | 9/2009 |

OTHER PUBLICATIONS

Patrice Desos et al: "Structure-activity relationships in a series of 2(1H)-quinolones bearing different acidic function in the 3-position: 6,7-dichloro-2(1H)-oxoquinoline-3-phosphonic acid, a new potent and selective AMPA/kainate antagonist with neuroprotective properties." Journal of Medicinal Chemistry, vol. 39, No. 1, 1996, pp. 197-206.

* cited by examiner

*Primary Examiner* — Janet Andres
*Assistant Examiner* — Timothy R Rozof
(74) *Attorney, Agent, or Firm* — James Cueva

(57) ABSTRACT

The present invention relates to novel herbicidal oxopyridine and thionopyridine derivatives of Formula (I), or an agronomically acceptable salt of said compound wherein $R^1$, $R^5$, $R^6$, $R^7$, $X^1$, $X^2$ and Q are as defined herein. The invention further relates to processes and intermediates for the preparation of the oxopyridine derivatives, to compositions which comprise the herbicidal compounds, and to their use for controlling weeds, in particular in crops of useful plants.

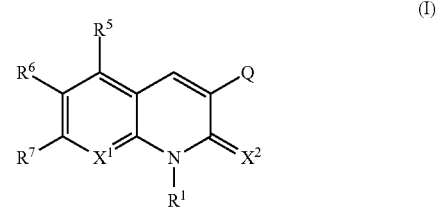

(I)

18 Claims, No Drawings

HERBICIDAL QUINOLINE AND 1,8-NAPHTHYRIDINE COMPOUNDS

This application is a 371 of International Application No. PCT/GB2010/000638 filed Mar. 31, 2010, which claims priority to GB 0905963.5 filed Apr. 6, 2009, and GB 0917407.9 filed Oct. 5, 2009, the contents of which are incorporated herein by reference.

The present invention relates to novel herbicidal oxopyridine and thionopyridine derivatives, to processes for their preparation, to compositions which comprise the herbicidal compounds, and to their use for controlling weeds, in particular in crops of useful plants, or for inhibiting plant growth.

According to the present invention there is provided a herbicidal compound of Formula (I):

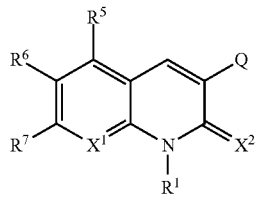

or an agronomically acceptable salt of said compound, wherein:

$R^1$ is selected from the group consisting of hydrogen, $C_1$-$C_6$alkyl, $C_1$-$C_6$haloalkyl, $C_1$-$C_3$alkoxy-$C_1$-$C_3$ alkyl, $C_1$-$C_3$alkoxy-$C_1$-$C_3$alkoxy-$C_1$-$C_3$-alkyl, $C_1$-$C_3$alkoxy-$C_1$-$C_3$-haloalkyl, $C_1$-$C_3$-alkoxy-$C_1$-$C_3$-alkoxy-$C_1$-$C_3$-haloalkyl, $C_4$-$C_6$-oxasubstituted cycloalkoxy-$C_1$-$C_3$-alkyl, $C_4$-$C_6$-oxasubstituted cycloalkyl-$C_1$-$C_3$-alkoxy-$C_1$-$C_3$-alkyl, $C_4$-$C_6$-oxasubstituted cycloalkoxy-$C_1$-$C_3$-haloalkyl, $C_4$-$C_6$-oxasubstituted cycloalkyl-$C_1$-$C_3$-alkoxy-$C_1$-$C_3$-haloalkyl, ($C_1$-$C_3$ alkanesulfonyl-$C_1$-$C_3$ alkylamino)-$C_1$-$C_3$ alkyl, ($C_1$-$C_3$alkanesulfonyl-$C_3$-$C_4$cycloalkylamino)-$C_1$-$C_3$alkyl, $C_1$-$C_6$alkylcarbonyl-$C_1$-$C_3$alkyl, $C_3$-$C_6$cycloalkyl-$C_2$-$C_6$alkenyl, $C_3$-$C_6$alkynyl, $C_2$-$C_6$-alkenyl, $C_2$-$C_6$-haloalkenyl, cyano-$C_1$-$C_6$-alkyl, arylcarbonyl-$C_1$-$C_3$-alkyl (wherein the aryl may be optionally substituted with one or more substituents from the group consisting of halo, $C_1$-$C_3$-alkoxy, $C_1$-$C_3$-alkyl, $C_1$-$C_3$ haloalkyl), aryl-$C_1$-$C_6$alkyl, aryloxy-$C_1$-$C_6$alkyl (wherein both cases the aryl may be optionally substituted with one or more substituents from the group consisting of halo, $C_1$-$C_3$-alkoxy, $C_1$-$C_3$-alkyl, $C_1$-$C_3$ haloalkyl), and a three- to ten-membered mono- or bicyclic ring system, which may be aromatic, saturated or partially saturated and can contain from 1 to 4 heteroatoms each independently selected from the group consisting of nitrogen, oxygen and sulphur the ring system being optionally substituted by one or more substituents selected from the group consisting of $C_1$-$C_3$alkyl, $C_1$-$C_3$haloalkyl, $C_1$-$C_3$alkenyl, $C_1$-$C_3$alkynyl, $C_1$-$C_3$ alkoxy, $C_1$-$C_3$ haloalkoxy, $C_1$-$C_6$alkyl-S(O)p-, $C_1$-$C_6$haloalkyl-S(O)p-, aryl, aryl-S(O)p, heteroaryl-S(O)p, aryloxy, heteroaryloxy, $C_1$-$C_3$ alkoxycarbonyl, $C_1$-$C_3$ alkylamino-S(O)p-, $C_1$-$C_3$ alkylamino-S(O)p-$C_1$-$C_3$ alkyl, $C_1$-$C_3$ dialkylamino-S(O)p-, $C_1$-$C_3$ dialkylamino-S(O)p-$C_1$-$C_3$ alkyl, $C_1$-$C_3$ alkylaminocarbonyl-, $C_1$-$C_3$ alkylaminocarbonyl-$C_1$-$C_3$ alkyl, $C_1$-$C_3$ dialkylaminocarbonyl, $C_1$-$C_3$ dialkylaminocarbonyl-$C_1$-$C_3$ alkyl, $C_1$-$C_3$ alkylcarbonylamino, $C_1$-$C_3$ alkyl-S(O)p-amino, cyano and nitro; the heteroaryl substituents containing one to three heteroatoms each independently selected from the group consisting of oxygen, nitrogen and sulphur, and wherein the aryl or heteroaryl component may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, phenyl, cyano and nitro;

$R^5$ is selected from the group consisting of hydrogen, chloro, fluoro and methyl;

$R^6$ is selected from the group consisting of hydrogen, fluorine, chlorine, hydroxyl and methyl;

$R^7$ is selected from the group consisting of hydrogen, cyano, nitro, halogen, hydroxyl, sulfhydryl, $C_1$-$C_6$alkyl, $C_3$-$C_6$cycloalkyl, $C_1$-$C_6$haloalkyl, $C_2$-$C_6$haloalkenyl, $C_2$-$C_6$alkenyl, aryl-$C_2$-$C_6$alkenyl, $C_3$-$C_6$alkynyl, $C_1$-$C_6$alkoxy, $C_4$-$C_7$ cycloalkoxy, $C_1$-$C_6$haloalkoxy, $C_1$-$C_6$alkyl-S(O)p, $C_3$-$C_6$cycloalkyl-S(O)p $C_1$-$C_6$haloalkyl-S(O)p, $C_3$-$C_6$ halocycloalkyl-S(O)p, $C_1$-$C_6$alkylcarbonylamino, ($C_1$-$C_6$alkylcarbonyl)$C_1$-$C_3$alkylamino, ($C_3$-$C_6$cycloalkylcarbonyl)amino, ($C_3$-$C_6$cycloalkylcarbonyl)$C_1$-$C_3$alkylamino, arylcarbonylamino, (arylcarbonyl)-$C_1$-$C_3$alkylamino, (heteroarylcarbonyl)amino, (heteroarylcarbonyl)$C_1$-$C_3$alkylamino, amino, $C_1$-$C_6$alkylamino, $C_2$-$C_6$dialkylamino, $C_2$-$C_6$alkenylamino, $C_1$-$C_6$alkoxy-$C_2$-$C_6$-alkylamino, ($C_1$-$C_6$alkoxy-$C_2$-$C_4$-alkyl)-$C_1$-$C_6$-alkylamino, $C_3$-$C_6$ cycloalkylamino, $C_3$-$C_6$ cyclohaloalkylamino, $C_1$-$C_3$alkoxy-$C_3$-$C_6$cycloalkylamino, $C_3$-$C_6$ alkynylamino, dialkylamino in which the substituents join to form a 4-6 membered ring (e.g pyrrolidinyl, piperidinyl) optionally containing oxygen (e.g morpholinyl) and/or optionally substituted by $C_1$-$C_3$-alkoxy and/or halogen (especially fluorine), $C_2$-$C_6$dialkylaminosulfonyl, $C_1$-$C_6$alkylaminosulfonyl, $C_1$-$C_6$alkoxy-$C_1$-$C_6$alkyl, $C_1$-$C_6$alkoxy-$C_2$-$C_6$alkoxy, $C_1$-$C_6$alkoxy-$C_2$-$C_6$alkoxy-$C_1$-$C_6$-alkyl, $C_3$-$C_6$alkenyl-$C_2$-$C_6$alkoxy, $C_3$-$C_6$alkynyl-$C_1$-$C_6$alkoxy, $C_1$-$C_6$alkoxycarbonyl, $C_1$-$C_6$alkylcarbonyl, $C_1$-$C_4$alkylenyl-S(O)p-R', $C_1$-$C_4$alkylenyl-$CO_2$—R', $C_1$-$C_4$alkylenyl-(CO)N—R'R', aryl (e.g. phenyl), aryl $C_1$-$C_3$alkyl, aryl-S(O)p, heteroaryl-S(O)p, aryloxy (e.g phenoxy), a 5 or 6-membered heteroaryl, heteroaryl $C_1$-$C_3$ alkyl and heteroaryloxy, the heteroaryl containing one to three heteroatoms, each independently selected from the group consisting of oxygen, nitrogen and sulphur, wherein the aryl or heteroaryl component may be optionally substituted by one or more substituents selected from the group consisting of $C_1$-$C_3$alkyl, $C_1$-$C_3$haloalkyl, $C_1$-$C_3$ alkoxy, $C_1$-$C_3$haloalkoxy, halo, cyano and nitro;

$X^1$=N—(O)n or C—$R^8$;

$X^2$=O or S;

n=0 or 1;

p=0, 1 or 2;

R' is independently selected from the group consisting of hydrogen and $C_1$-$C_6$alkyl;

$R^8$ is selected from the group consisting of hydrogen, halogen, $C_1$-$C_6$alkyl, $C_1$-$C_6$haloalkyl, $C_1$-$C_6$alkylcarbonyl-$C_1$-$C_3$alkyl, $C_3$-$C_6$cycloalkyl-$C_2$-$C_6$alkenyl for example cyclohexylmethylenyl, $C_3$-$C_6$alkynyl (for example propargyl), $C_2$-$C_6$-alkenyl (for example allyl), $C_1$-$C_6$alkoxy $C_1$-$C_6$alkyl, cyano-$C_1$-$C_6$-alkyl, arylcarbonyl-$C_1$-$C_3$-alkyl (wherein the aryl may be optionally substituted with one or more substituents selected from the group consisting of halo, $C_1$-$C_3$-alkoxy, $C_1$-$C_3$-alkyl, $C_1$-$C_3$ haloalkyl), aryl-$C_1$-$C_6$alkyl (wherein the aryl may be optionally substituted with one or more substituents from the group consisting of halo, $C_1$-$C_3$-alkoxy, $C_1$-$C_3$-alkyl, $C_1$-$C_3$ haloalkyl), $C_1$-$C_6$alkoxy$C_1$-$C_6$alkoxy $C_1$-$C_6$alkyl, aryl, a 5 or 6-membered heteroaryl, a 5 or 6-membered heteroaryl-$C_1$-$C_3$-alkyl and heterocyclyl-$C_1$-$C_3$-alkyl, the heteroaryl or heterocyclyl containing one to three heteroatoms each independently selected from the group consisting of oxygen, nitrogen and sulphur, and wherein the aryl, heterocyclyl or heteroaryl component may be optionally substituted by one or more substituents from the group consisting of halogen, $C_1$-$C_3$alkyl, $C_1$-$C_3$haloalkyl and $C_1$-$C_3$ alkoxy, cyano and nitro;

Q is selected from the group consisting of:—

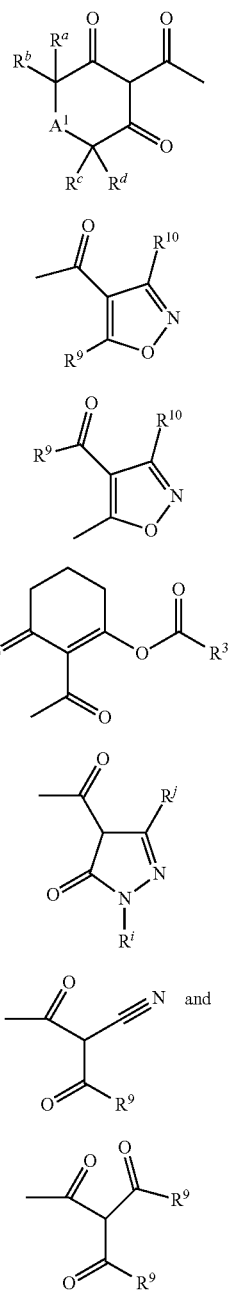

wherein
$A^1$ is selected from the group consisting of O, C(O), S, SO, $SO_2$ and $(CR^eR^f)_q$;
q=0, 1 or 2;
$R^a$, $R^b$, $R^c$, $R^d$, $R^e$ and $R^f$ are each independently selected from the group consisting of $C_1$-$C_4$alkyl which may be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfonyl, $C_1$-$C_4$alkylcarbonyl, phenyl and heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, the substituents on the nitrogen in the heterocyclic ring being other than halogen; or $R^a$, $R^b$, $R^c$, $R^d$, $R^e$ and $R^f$ are each independently selected from the group consisting of hydrogen, $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, the substituents on the nitrogen in the heterocyclic ring being other than halogen; or $R^a$ and $R^b$ together form a 3- to 5-membered carbocyclic ring which may be substituted by $C_1$-$C_4$alkyl and may be interrupted by oxygen, sulfur, S(O), $SO_2$, OC(O), $NR^g$ or by C(O); or $R^a$ and $R^c$ together form a $C_1$-$C_3$alkylene chain which may be interrupted by oxygen, sulfur, SO, $SO_2$, OC(O), Me or by C(O); it being possible for that $C_1$-$C_3$alkylene chain in turn to be substituted by $C_1$-$C_4$alkyl;

$R^g$ and $R^h$ are each independently of the other $C_1$-$C_4$alkyl, $C_1$-$C_4$haloalkyl, $C_1$-$C_4$alkylsulfonyl, $C_1$-$C_4$alkylcarbonyl or $C_1$-$C_4$alkoxycarbonyl;

$R^i$ is $C_1$-$C_4$alkyl;

$R^j$ is selected from the group consisting of hydrogen, $C_1$-$C_4$ alkyl and $C_3$-$C_6$ cycloalkyl;

$R^3$ is selected from the group consisting of $C_1$-$C_6$alkyl, optionally substituted with halogen and/or $C_1$-$C_3$alkoxy, and $C_3$-$C_6$ cycloalkyl optionally substituted with halogen and/or $C_1$-$C_3$alkoxy;

$R^9$ is selected from the group consisting of cyclopropyl, $CF_3$ and i.-Pr;

$R^{10}$ is selected from the group consisting of hydrogen, I, Br, $SR^{11}$, $S(O)R^{11}$, $S(O)_2R^{11}$ and $CO_2R^{11}$; and $R^{11}$ is $C_{1-4}$ alkyl.

Halogen encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Suitable alkylenyl radicals include, for example $CH_2$, $CHCH_3$, $C(CH_3)_2$, $CH_2CHCH_3$, $CH_2CH(C_2H_5)$.

Suitable haloalkenyl radicals include alkenyl groups substituted one or more times by halogen, halogen being fluorine, chlorine, bromine or iodine and especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Preferred $C_2$-$C_6$alkenyl radicals substituted once, twice or three times by halogen are those having a chain length of from 2 to 5 carbon atoms. Suitable haloalkylalkynyl radicals include, for example, alkylalkynyl groups substituted one or more times by halogen, halogen being bromine or iodine and, especially, fluorine or chlorine, for example 3-fluoropropynyl, 5-chloropent-2-yn-1-yl, 5-bromopent-2-yn-1-yl, 3,3,3-trifluoropropynyl and 4,4,4-trifluoro-but-2-yn-1-yl. Preferred alkylalkynyl groups substituted one or more times by halogen are those having a chain length of from 3 to 5 carbon atoms.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl, preferably methoxycarbonyl, ethoxycarbonyl or tert-butoxycarbonyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino is, for example, methylamino, ethylamino, n-propylamino, isopropylamino or a butylamino isomer. Dialkylamino is, for example, dimethylamino, methylethylamino, diethylamino, n-propylmethylamino, dibutylamino or diisopropylamino. Preference is given to alkylamino groups having a chain length of from 1 to 4 carbon atoms.

Cycloalkylamino or dicycloalkylamino is for example cyclohexylamino or dicyclopropylamino.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthioalkyl groups preferably have from 1 to 6 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl.

Three- to ten-membered mono- or bicyclic ring system may be aromatic, saturated or partially saturated and can contain from 1 to 4 heteroatoms each independently selected from the group consisting of nitrogen, oxygen and sulphur the ring system being optionally substituted by one or more substituents independently selected from the group consisting of $C_1$-$C_3$alkyl, $C_1$-$C_3$haloalkyl, $C_1$-$C_3$alkenyl, $C_1$-$C_3$alkynyl, $C_1$-$C_3$ alkoxy, $C_1$-$C_3$ haloalkoxy, $C_1$-$C_6$alkyl-S(O)p-, $C_1$-$C_6$haloalkyl-S(O)p-, aryl, aryl-S(O)p, heteroaryl-S(O)p, aryloxy, heteroaryloxy, $C_1$-$C_3$ alkoxycarbonyl, $C_1$-$C_3$ alkylamino-S(O)p-, $C_1$-$C_3$ alkylamino-S(O)p-$C_1$-$C_3$ alkyl, $C_1$-$C_3$ dialkylamino-S(O)p-, $C_1$-$C_3$ dialkylamino-S(O)p-$C_1$-$C_3$ alkyl, $C_1$-$C_3$ alkylaminocarbonyl-, $C_1$-$C_3$ alkylaminocarbonyl-$C_1$-$C_3$ alkyl, $C_1$-$C_3$ dialkylaminocarbonyl, $C_1$-$C_3$ dialkylaminocarbonyl-$C_1$-$C_3$ alkyl, $C_1$-$C_3$ alkylcarbonylamino, $C_1$-$C_3$ alkyl-S(O)p-amino, cyano and nitro. Such ring systems thus include, for example, cycloalkyl, phenyl, heterocyclyl and heteroaryl. Examples of "partially saturated" rings include, for example, 1,4 benzodioxin and 1,3 benzodioxole.

Cycloalkyl groups preferably have from 3 to 6 ring carbon atoms and may be substituted by one or more methyl groups; they are preferably unsubstituted, for example cyclopropyl, cyclobutyl, cyclopentyl or cyclohexyl.

Aryl includes benzyl, phenyl, including phenyl as part of a substituent such as phenoxy, benzyl, benzyloxy, benzoyl, phenylthio, phenylalkyl, phenoxyalkyl or tosyl, may be in mono- or poly-substituted form, in which case the substituents may, as desired, be in the ortho-, meta- and/or para-position(s).

Heterocyclyl, for example, includes morpholinyl, tetrahydrofuryl.

Heteroaryl, including heteroaryl as part of a substituent such as heteroaryloxy, means, for example, a five or six member heteroaryl containing one to three heteroatoms, each independently selected from the group consisting of oxygen, nitrogen and sulphur. It should be understood that the heteroaryl component may be optionally mono or poly substituted. The term heteroaryl thus includes, for example, furanyl, thiophenyl, thiazolyl, oxazolyl, isoxazolyl, thiazolyl, pyrazolyl, isothiazolyl, pyridyl, pyridazinyl, pyrazinyl, pyrimidinyl, triazolyl.

Compounds of Formula I may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula I comprising Q1, Q5, Q6 or Q7 or when $R^1$ is hydrogen may be in equilibrium with alternative hydroxyl tautomeric forms. It should be appreciated that all tautomeric forms (single tautomer or mixtures thereof), racemic mixtures and single isomers are included within the scope of the present invention.

The skilled person will also appreciate that if n is 1 with regard to Formula I to form the N-oxide then the nitrogen and oxygen will be charged accordingly ($N^+O^-$).

In a preferred embodiment of the present invention $X^2$ is oxygen.

In another preferred embodiment $R^1$ is selected from the group consisting of hydrogen, $C_1$-$C_6$alkyl, $C_1$-$C_6$haloalkyl, $C_1$-$C_3$alkoxy$C_1$-$C_3$alkyl, $C_1$-$C_3$alkoxy $C_2$-$C_3$alkoxy$C_1$-$C_3$alkyl, $C_1$-$C_6$haloalkyl, $C_2$-$C_6$haloalkenyl $C_1$-$C_3$alkoxy-$C_1$-$C_3$haloalkyl and phenyl.

In another preferred embodiment $R^1$ is aryl, preferably phenyl, or a 5 or 6-membered heteroaryl containing one to three heteroatoms each independently selected from the group consisting of oxygen, nitrogen and sulphur, and wherein the aryl or heteroaryl may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)p-, $C_1$-$C_6$haloalkyl-S(O)p-, cyano and nitro. Especially preferred is wherein $R^1$ is an optionally substituted aryl selected from the group consisting of phenyl, phenoxy, phenoxy-$C_1$-$C_6$alkyl, benzyl, thiophenyl, 1,4 benzodioxinyl, 1,3 benzodioxoleyl and pyridyl.

In another preferred embodiment $R^5$ is hydrogen or methyl.

In another preferred embodiment $R^6$ is hydrogen or fluorine.

In another preferred embodiment $R^3$ is selected from the group consisting of hydrogen, methyl and cyclopropyl.

In another preferred embodiment the herbicidal compound is of Formula (Ia):

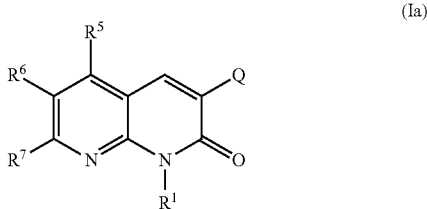

(Ia)

In a more preferred embodiment of the present invention the herbicidal compound is of Formula (Ia) wherein Q is Q1, in particular wherein $A^1$ is $CR^eR^f$ and wherein $R^a$, $R^b$, $R^c$, $R^d$, $R^e$ and $R^f$ are hydrogen, and wherein q=1. In another preferred embodiment of the present invention Q is Q1, wherein $A^1$ is $CR^eR^f$ and wherein, $R^b$, $R^d$, $R^e$ and $R^f$ are hydrogen, $R^a$ and $R^e$ together form an ethylene chain and wherein q=1

In another preferred embodiment, when the herbicidal compound is of Formula (Ia) and wherein $R^7$ is selected from the group consisting of hydrogen, hydroxyl, halogen, $C_1$-$C_6$alkyl, $C_3$-$C_6$cycloalkyl, $C_1$-$C_6$haloalkyl, $C_1$-$C_6$ alkoxy, $C_1$-$C_6$ alkoxy-$C_2$-$C_6$-alkoxy, $C_1$-$C_6$-alkoxy-$C_1$-$C_6$ alkyl, $C_1$-$C_6$-alkoxy-$C_2$-$C_6$-alkoxy-$C_1$-$C_6$ alkyl, $C_1$-$C_6$alkylamino, $C_1$-$C_6$dialkylamino, $C_2$-$C_6$alkenylamino, $C_1$-$C_6$alkoxy-$C_2$-$C_3$-alkylamino, ($C_1$-$C_6$alkoxy-$C_2$-$C_4$-alkyl)-$C_1$-$C_6$-alkylamino, $C_3$-$C_6$ cycloalkylamino, $C_3$-$C_6$ cyclohaloalkylamino, $C_1$-$C_3$alkoxy-$C_3$-$C_6$ cycloalkylamino, $C_3$-$C_6$ alkynylamino and dialkylamino group in which the substituents join to form a 4-6 membered ring, optionally containing oxygen, and/or optionally substituted by $C_1$-$C_3$-alkoxy and/or halogen, especially fluorine, In an even more preferred embodiment $R^7$ is selected from the group consisting of hydrogen, fluoro, bromo, chloro, methyl, ethyl, 1-methylethyl, cyclopropyl, fluoromethyl, 1-fluoroethyl, 1,1-difluoroethyl, 2,2-difluoroethyl, 1-fluoro-1-methylethyl, 2,2,2-trifluoroethyl, difluorochloromethyl, methoxy, ethoxy, methoxymethyl, 1-methoxyethyl, 2-methoxyethoxy, 2-methoxyethoxymethyl, (2-methoxyethyl)amino and (2-methoxyethyl)methylamino. Hydrogen and methyl are particularly preferred.

In another preferred embodiment the herbicidal compound is of Formula (Ib):

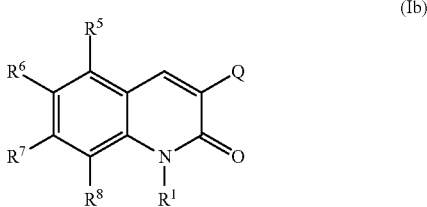

(Ib)

In another preferred embodiment of the present invention the herbicidal compound is of Formula (Ib), wherein Q is Q1, in particular wherein $A^1$ is $CR^eR^f$ and wherein $R^a$, $R^b$, $R^c$, $R^d$, $R^e$ and W are hydrogen, and wherein q=1. In another preferred embodiment of the present invention Q is Q1, wherein $A^1$ is $CR^eR^f$ and wherein, le, $R^d$, $R^e$ and $R^f$ are hydrogen, $R^a$ and $R^e$ together form an ethylene chain and wherein q=1.

In another preferred embodiment wherein the herbicidal compound is of Formula (Ib) and wherein $R^7$ is selected from the group consisting of hydrogen, cyano, halogen, nitro, $C_1$-$C_6$haloalkyl, $C_1$-$C_3$ alkoxy$C_1$-$C_3$ haloalkyl, $C_1$-$C_3$ alkoxy$C_2$-$C_6$-alkoxy$C_1$-$C_3$haloalkyl, $C_1$-$C_6$haloalkoxy, $C_1$-$C_6$alkylS(O)p, $C_3$-$C_6$cycloalkylS(O)p $C_1$-$C_6$haloalkyl-S(O)p, $C_3$-$C_6$halocycloalkyl-S(O)p, aryl-S(O)p and heteroaryl-S(O)p. In an even more preferred embodiment $R^7$ is selected from the group consisting of chloro, fluoro, cyano, nitro, fluoromethyl, difluoromethyl, trifluoromethyl, 1-fluoroethyl, 1,1-difluoroethyl, 1-fluoro-1-methylethyl, difluorochloromethyl, difluoromethoxy, trifluoromethoxy, 1,1-difluoroethoxy, methylsulfinyl, methylsulfonyl, ethylsulfinyl, ethylsulfonyl, phenyl sulfinyl and phenyl sulfonyl.

The present invention also includes agronomically acceptable salts that the compounds of Formula I may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-allcylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonyiphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, T+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+triallate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1- methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), I+4-hydroxy-3-[[2-[(2-methoxyethoxy)methyl]-6-(trifluoro-methyl)-3-pyridinyl]carbonyl]-bicyclo[3.2.1]oct-3-en-2-one (CAS RN 352010-68-5), and I+4-hydroxy-3-[[2-(3-methoxypropyl)-6-(difluoromethyl)-3-pyridinyl]carbonyl]-bicyclo[3.2.1]oct-3-en-2-one. The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Fourteenth Edition, British Crop Protection Council, 2006.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, and N-isopropyl-4-(2-methoxy-benzoylsulfamoyl)-benzamide (CAS RN 221668-34-4). Other possibilities include safener compounds disclosed in, for example, EP0365484. Particularly preferred are mixtures of a compound of Formula I with cyprosulfamide, isoxadifen-ethyl and/or cloquintocet-mexyl.

The safeners of the compound of Formula I may also be in the form of esters or salts, as mentioned e.g. in The Pesticide Manual, $14^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf. Maize is particularly preferred.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

In a preferred embodiment the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared using the following methods.

Preparation of compounds of the present invention is outlined in the following schemes.

Preparation of compounds Formula (I)

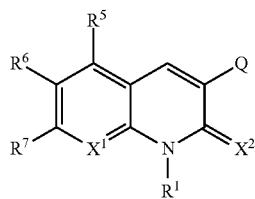

(I)

where Q is selected from Q1 and Q5 is carried out analogously to known processes (for example those described in WO97/46530, EP0353187 and U.S. Pat. No. 6,498,125) and comprises reacting a compound of the following formula:

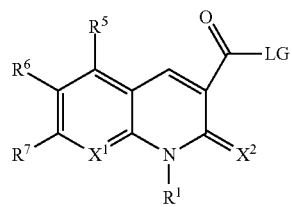

where the definitions $R^1$, $R^5$, $R^6$, $R^7$, $X^1$ and $X^2$ are as for Formula (I) and LG is a suitable leaving group, for example a halogen atom, such as chlorine, or an alkoxy or aryloxy group, such as 4-nitrophenoxy, in an inert organic solvent, such as dichloromethane or acetonitrile, in the presence of a base, such as triethylamine, with compounds

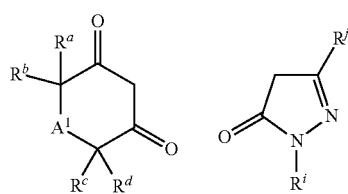

wherein
$A^1$ and $R^a$, $R^b$, $R^c$, $R^d$, $R^e$, $R^f$ and $R^i$, $R^j$ are as defined previously;

to give the following esters (3a) or (3b):

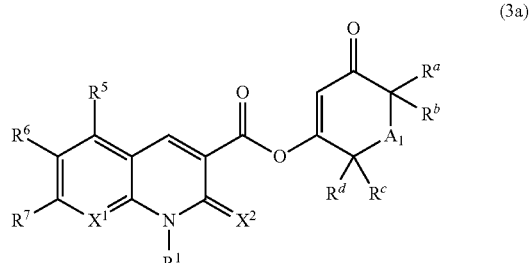

(3a)

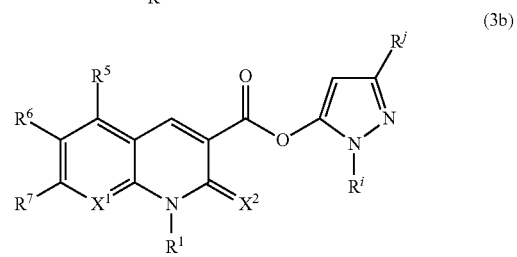

(3b)

which may be rearranged using catalysts, such as 4-dimethylaminopyridine, or acetone cyanhydrin, or a metal cyanide salt, such as sodium cyanide, in the presence of a suitable base, such as triethylamine, to give compounds of Formula (I). It is advantageous to have a dehydrating agent, such as molecular sieves, present in the reaction medium to ensure any water initially present in the solvent or associated with the other components of the reaction mixture is prevented from causing any unwanted hydrolysis of intermediates.

Scheme 1

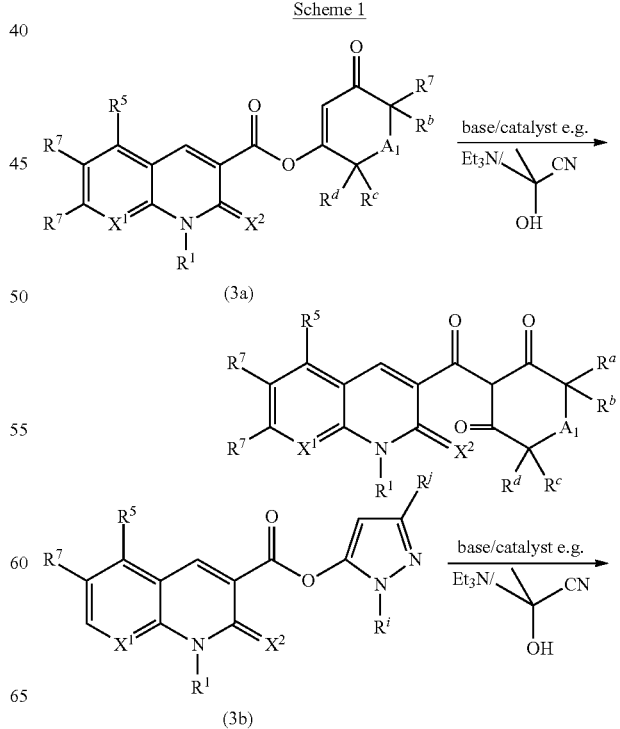

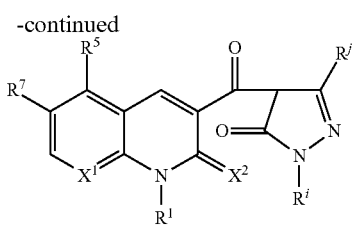

2-oxo or 2-thiono pyridine-3-carboxylic acid derivatives of Formulae 3a and 3b may be prepared from the corresponding 3-carboxylic acids, for example by reaction with a suitable halogenating agent, such as oxalyl chloride, in a suitable inert solvent, such as dichloromethane, to generate the corresponding 3-carboxylic acid chlorides. These derivatives may in turn be reacted with, for example, 4-nitrophenol and a suitable base, such as triethylamine, in an inert solvent, such as dichloromethane, to generate the corresponding 4-nitrophenyl esters.

By way of illustration as shown in Scheme 2, 2-oxo-pyridine-3-carboxylic acid esters or 2-thionoy-pyridine-3-carboxylic acid esters of Formula 4a or Formula 4b may be obtained from 2-amino-benzaldehydes and 2-amino-3-formylpyridines analogous to methods described in the literature.

The required 2-aminobenzaldehydes and 2-amino-3-formylpyridines and are either commercially available or may be prepared by methods described in the literature for example *Comptes Rendus des Seances de l'Academie des Sciences, Serie C: Sciences Chinziques* (1975), 280(6), 381-3, *J. Org. Chem.* (1983), 48, 3401-3408, *J. Org. Chem.* (1990), 55, 4744-4750 and *Org. Letts.*, (2002), 4, (20) 3481-3484, *Synthesis* (2008) 2674-2770 or by analogous methods.

By way of illustration as shown in Scheme 3, optionally substituted 2-aminopyridines may be N-acylated, for example with a suitable acylating reagent, such as acetyl chloride or pivaloyl chloride, and a suitable base, such as triethylamine, optionally with a suitable acylation catalyst such as 4-dimethylaminopyridine, in an inert solvent, such as dichloromethane, to give the corresponding N-(pyridin-2-yl) amides. Analogous to methods described in the literature, these amides may in turn be reacted with a strong base, such as n.butyllithium or t.butyl lithium and then a formyl transfer agent, such as N,N-dimethylformamide or N-formyl-N-methylaniline, to give the corresponding N-(3-formylpyridin-2-yl)amides. The required 2-amino-3-formylpyridines can be obtained by hydrolysis of these amides using, for example, aqueous hydrochloric acid heated under reflux for 1 to 24 hours.

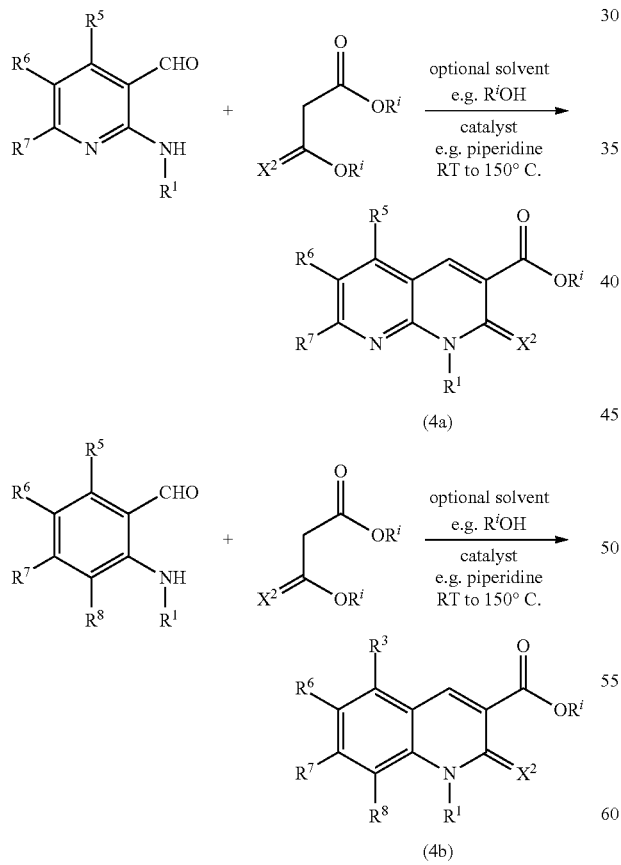

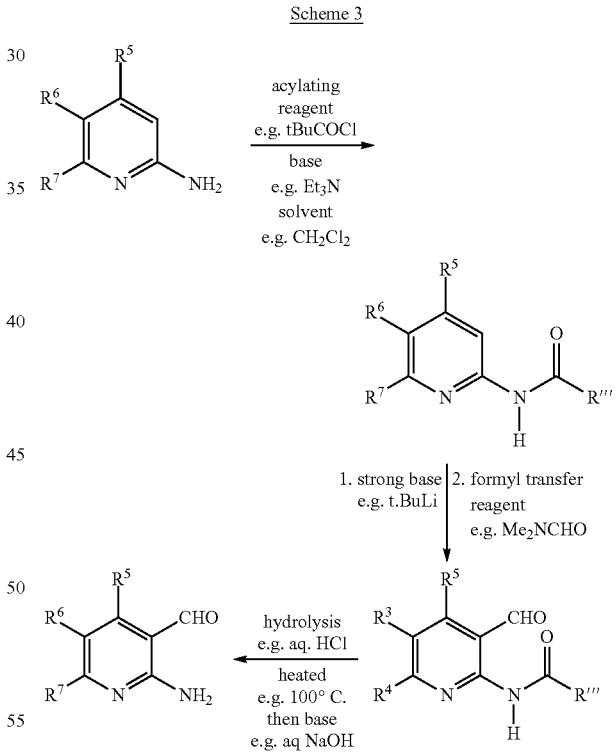

The required malonate esters are either commercially available or may be prepared analogously to methods described in the literature, for example *Can. J. Chem.* (1968), 46, 2251.

With regard to scheme 3, R''' is for example, $C_1$-$C_6$ alkyl.

Alternatively, as shown in Scheme 4, 2-aminopyridine-3-carboxylic esters may be reduced, using a suitable reducing agent, such as lithium aluminium hydride, in a suitable solvent, such as tetrahydrofuran, to 2-amino-3-hydroxymethylpyridines and subsequently oxidised, using a suitable oxidising agent, such as manganese dioxide, in a suitable solvent, such as dichloromethane, to the required 2-amino-3-formylpyridines.

Scheme 4

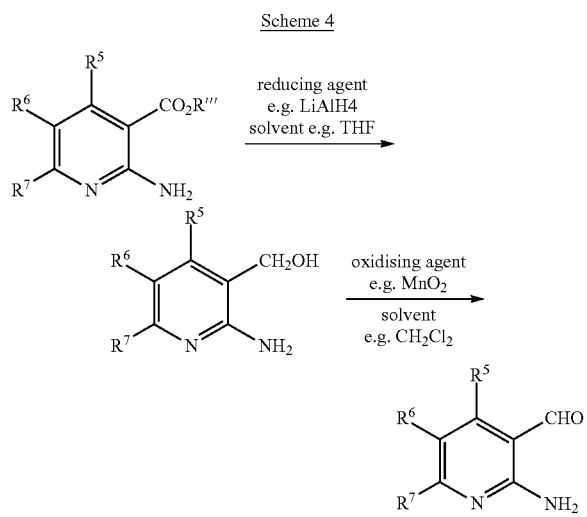

Alternatively, as shown in Scheme 4a, a pyridine aldehyde substituted on the amino group ($R^1$ not=H) may be prepared from a pyridine aldehyde ($R^1$=H) by N-substitution with an aryl or heteroaryl bromide in the presence of a suitable palladium catalyst and ligand, for example Pd2(dba)3 and *Xantphos*, in a suitable solvent such as dioxane, in the presence of a base, such as caesium carbonate.

Scheme 4a

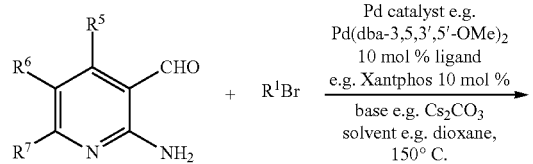

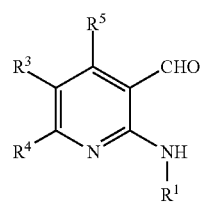

Alternatively as shown in Scheme 4b, a pyridine aldehyde substituted on the amino group ($R^1$ not =H) may be prepared from a 2-chloro-pyridine aldehyde by reaction with an amine, for example in the presence of a suitable palladium catalyst and ligand, for example Pd2(dba)3 and *Xantphos*, in a suitable solvent such as dioxane, in the presence of a base, such as caesium carbonate.

Scheme 4b

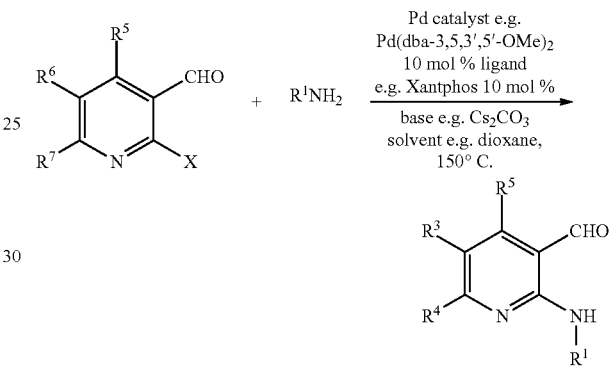

As shown in Scheme 5, 2-oxopyridine ester derivatives where $R^1$ is hydrogen, may be further reacted with alkylating agents or arylating or heteroarylating agents using procedures described in the literature (for example *Tetrahedron*, (1999), 55, 12757-12770 or by analogous procedures).

Scheme 5

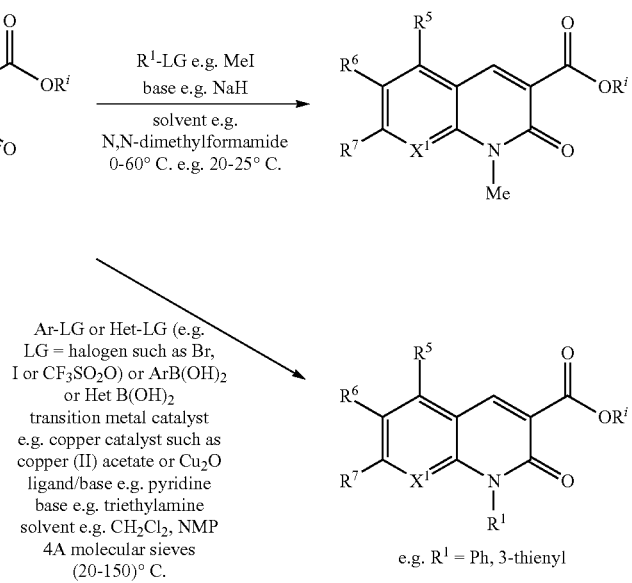

As shown in Scheme 6, pyridyl-3-carboxylic acid esters derivatives of Formula 6 may be conveniently hydrolysed to the corresponding carboxylic acids (7) using standard procedures, for example using aqueous sodium hydroxide and a co-solvent such as ethanol, or lithium hydroxide in aqueous tetrahydrofuran.

Scheme 6

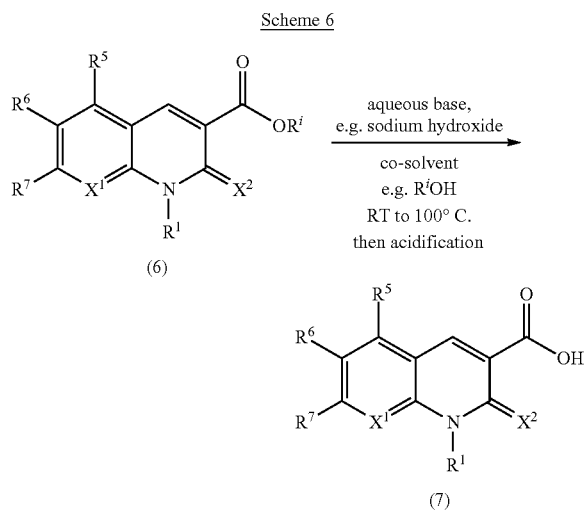

As shown in Scheme 7, 2-oxopyridyl-3-carboxylic acid esters of Formula 8 may be conveniently converted to the corresponding N-oxides using a suitable oxidant, such as a peracid, for example per-trifluoroacetic acid generated from urea hydrogen peroxide complex and trifluoroacetic acid anhydride.

The N-oxides generated may be further reacted with a suitable acid halide reagent, such as phosphoryl chloride, optionally with a suitable base, such as triethylamine, in a suitable solvent, such as dichloromethane or 1,2-dichloroethane, at 20° C. to 100° C. to give the 7-halo derivatives.

Scheme 7

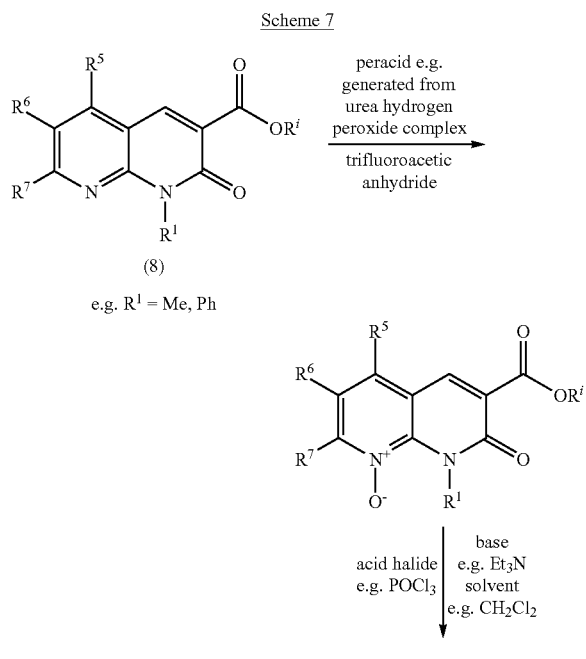

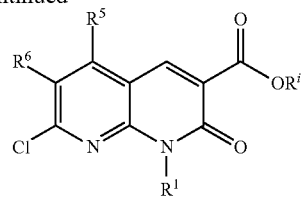

With regard to Scheme 7, $R^i$ is, for example, $C_1$-$C_4$ alkyl.

As shown in Scheme 8, 7-halo-2-oxo or 7-halo-2-thiono-[1,8]-naphthyridines may be further transformed into additional 7-substituted-2-oxo or 2-thiono-[1,8]-naphthyridines useful for preparing compounds of Formula (I). For example, when $R^5$ is hydrogen or methyl and $R^7$ is a chlorine atom, the chlorine may be displaced by an alkoxide reagent, such as sodium ethoxide, in a suitable solvent, such as tetrahydrofuran or N,N-dimethylformamide or an alcohol, such as ethanol, to generate the corresponding 7-alkoxy-2-oxo or 7-alkoxy-2-thiono-[1,8]-naphthyridine derivative. Similarly, 7-halo-2-oxo- or 7-halo-2-thiono-[1,8]-naphthyridines may be reacted with an amine, such as morpholine, in a suitable solvent, such as tetrahydrofuran, to generate the corresponding 7-alkylamino-2-oxo- or 7-alkylamino-2-thiono-[1,8]-naphthyridines or 7-dialkylamino-2-oxo- or 7-dialkylamino-2-thiono-[1,8]-naphthyridines. Additionally, 7-halo-2-oxo or 7-halo-2-thiono-[1,8]-naphthyridines, such as 7-chloro-2-oxo or 7-chloro-2-thiono-[1,8]-naphthyridines, 7-alkoxy-2-oxo or 7-alkoxy-2-thiono-[1,8]-naphthyridines, such as 7-methoxy-2-oxo or 7-methoxy-2-thiono-[1,8]-naphthyridines, may be converted to 7-hydroxy-2-oxo or 7-hydroxy-2-thiono-[1,8]-naphthyridines, for example by hydrolysis under acidic conditions, such as heating with aqueous hydrochloric acid. Such reactions may be conducted at temperatures from 20° C. to 150° C., for example in a microwave oven. Additionally, 7-hydroxy-2-oxo or 7-hydroxy-2-thiono-[1,8]-naphthyridines may be transformed to the corresponding 7-haloalkanesulfonate esters of [1,8]naphthyridines, such as 2-oxo or 2-thiono-7-trifluoromethanesulfonyloxy[1,8] naphthyridines, with a suitable acylation agent, such as trifluoromethane sulfonic anhydride, and a suitable base, such as triethylamine, in a suitable solvent, such as dichloromethane. In another aspect, 7-halo-2-oxo or 7-halo-2-thiono-[1,8]-naphthyridines, such as 7-chloro-2-oxo or 7-chloro-2-thiono-[1,8]-naphthyridines, or 7-haloalkanesulfonate esters of [1,8] naphthyridines, such as 2-oxo or 2-thiono-7-trifluoromethanesulfonyloxy[1,8]naphthyridines, may be reacted with an alkyl or aryl or heteroaryl boronic acid reagent, such as methyl boronic acid or phenyl boronic acid or 3-thienylboronic acid, in the presence of a palladium catalyst, such as palladium acetate, and a suitable base such as potassium phosphate and a suitable palladium ligand, such as dicyclohexyl-(2',6'-dimethoxybiphenyl-2-yl) phosphane, to generate 7-methyl or 7-phenyl or 7-(thienyl-3-yl) 2-oxo- or 2-thiono[1,7]naphthyridine derivatives.

Scheme 8

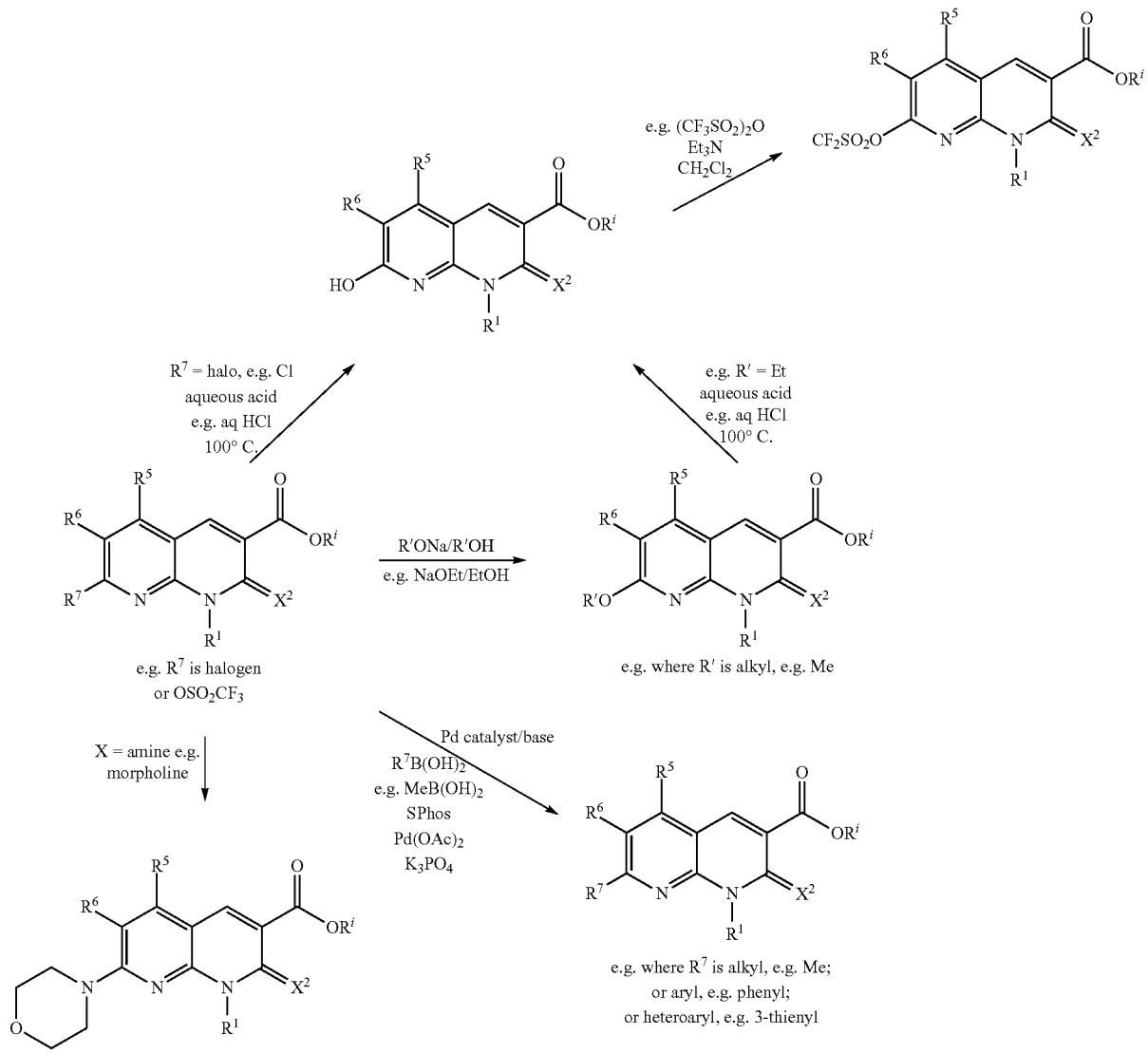

EXAMPLES

Abbreviations as used in the following Examples are as follows: s=singlet, d=doublet, t=triplet, m=multiplet, bs=broad signal, bm=broad multiplet, dd=double doublet, dt=double triplet, td=triple doublet and dq=double quartet.

Example 1

Preparation of 2-(6-fluoro-2-oxo-1,2-dihydro[1,8]-naphthyridine-3-carbonyl)-cyclohexane-1,3-dione Stage 1

Preparation of N-(5-fluoro-pyridin-2-yl)-2,2-dimethylpropionamide

To a stirred solution of 2-amino-5-fluoropyridine (50.0 g, commercially available) and triethylamine (93 ml) in dichloromethane (600 ml) was added pivaloyl chloride (56 ml) at ambient temperature. The slurry that formed was stirred for 3 hours, stored for 18 hours then washed with water (200 ml), brine (100 ml) then dried over magnesium sulfate, filtered and evaporated under reduced pressure to give the required product as a brown oil, 86 g. $^1$H NMR (CDCl$_3$) δ: 8.30 (1H, dd), 8.10 (1H, d), 8.00 (1H, bs), 7.42 (1H, m), 1.30 (9H, s).

In a similar procedure, N-(6-methylpyridin-2-yl)-2,2-dimethylpropionamide was prepared from 2-amino-6-methylpyridine. $^1$H NMR (CDCl$_3$) δ: 8.02-8.04 (1H, d), 7.95 (1H, broad s), 7.54-7.60 (1H, t), 6.86-6.88 (1H, d), 2.44 (3H, s), 1.31 (9H, s). Similarly, N-(5-fluoro-6-methylpyridin-2-yl)-2,2-dimethylpropionamide was prepared from 2-amino-5-fluoro-6-methylpyridine. $^1$H NMR (CDCl$_3$) δ: 8.02 (1H, dd), 7.95 (1H, broad s), 7.35 (1H, t), 2.44 (3H, d), 1.32 (9H, s).

Stage 2

Preparation of N-(5-fluoro-3-formyl-pyridin-2-yl)-2,2-dimethylpropionamide

To a stirred solution of N-(5-fluoro-pyridin-2-yl)-2,2-dimethylpropionamide (39.2 g) in dry diethyl ether (1200 ml)

under an atmosphere of nitrogen at −78° C. was added dropwise t.-butyl lithium in hexanes (1.7M, 300 ml). The mixture was stirred at −78° C. for 2 hours then dry N,N-dimethylformamide (160 ml) was added and the slurry stirred at −78° C. for 1 hour then allowed to slowly warm to ambient temperature and stirred for an additional 1 hour. The mixture was quenched with aqueous 2M hydrochloric acid until a clear biphasic solution was formed and the organic phase separated. The aqueous phase was further extracted with diethyl ether. The extracts were combined, washed with brine (300 ml), dried over magnesium sulfate, filtered and evaporated under reduced pressure to give the required product as a pale yellow solid, 40 g. $^1$H NMR (CDCl$_3$) δ: 11.20 (1H, s), 9.94 (1H, s), 8.59 (1H, d), 7.84 (1H, dd), 1.42 (9H, s).

In a similar procedure, N-(3-formyl-6-methylpyridin-2-yl)-2,2-dimethylpropionamide was prepared from N-(6-methylpyridin-2-yl)-2,2-dimethylpropionamide $^1$H NMR (CDCl$_3$) δ: 10.9 (1H, broad s), 9.88 (1H, s), 7.89-7.91 (1H, d), 7.03-7.05 (1H, d), 2.64 (3H, s), 1.38 (9H, s).

Similarly, N-(5-fluoro-3-formyl-6-methylpyridin-2-yl)-2,2-dimethylpropionamide was prepared from N-(5-fluoro-6-methylpyridin-2-yl)-2,2-dimethylpropionamide $^1$H NMR (CDCl$_3$) δ: 10.15 (1H, s), 9.82 (1H, s), 7.68 (1H, d), 2.60 (3H, d), 1.38 (9H, s), Similarly, N-(3-formyl-6-methoxymethylpyridin-2-yl)-2,2-dimethylpropionamide was prepared from N-(6-methoxymethylpyridin-2-yl)-2,2-dimethylpropionamide, brown oil, $^1$H NMR (CDCl$_3$) δ: 9.91 (1H, s), 8.04 (1H, d), 7.36 (1H, d), 4.66 (2H, s), 3.51 (3H, s), 1.37 (9H, s).

Stage 3

Preparation of 2-amino-5-fluoropyridinyl-3-carboxaldehyde

A mixture of N-(5-fluoro-3-formyl-pyridin-2-yl)-2,2-dimethylpropionamide (14.2 g) in aqueous 2M hydrochloric acid (200 ml) was stirred at 100° C. for 45 minutes, cooled to ambient temperature, treated with sodium hydrogen carbonate until the mixture was pH 5 then extracted with dichloromethane (2×100 ml). The extracts were combined, washed with aqueous sodium hydrogen carbonate (50 ml) then water (50 ml), dried over magnesium sulfate, filtered and evaporated under reduced pressure to give the required product as a yellow solid, 6.5 g. $^1$H NMR (CDCl$_3$) δ: 9.82 (1H, s), 8.18 (1H, d), 7.54 (1H, dd), 6.62 (2H, bs).

In a similar procedure, 2-amino-6-methylpyridinyl-3-carboxaldehyde was prepared from N-(3-formyl-6-methylpyridin-2-yl)-2,2-dimethylpropionamide, $^1$H NMR (CDCl$_3$) δ: 9.80 (1H, s), 7.68-7.70 (1H, d), 6.56-6.58 (1H, d), 2.42 (3H, s).

Similarly, 2-amino-5-fluoro-6-methylpyridinyl-3-carboxaldehyde was prepared from N-(5-fluoro-3-formyl-6-methylpyridin-2-yl)-2,2-dimethylpropionamide, $^1$H NMR (CDCl$_3$) δ: 9.78 (1H, s), 7.43 (1H, d), 2.42 (3H, d).

Other carboxaldehydes useful in the present invention can be prepared, for example, in the following manner.

Preparation of 5-fluoro-2-(2-trifluoromethyl-phenylamino)-pyridine-3-carboxyaldehyde A mixture of 2-amino-5-fluoro-pyridine-3-carbaldehyde (680 mg), 2-bromo-trifluoromethylbenzene (1.02 ml), Pd(dba-3,5,3',5'-OMe)$_2$ (407 mg), Xantphos (290 mg) and caesium carbonate (2.28 g) in dioxane (10 ml) was heated at 150° C. in the microwave for 30 minutes. The reaction mixture was allowed to cool to room temperature, filtered, then evaporated under reduced pressure. The residue was purified by column chromatography (silica; ethyl acetate/hexane) to give the required product as a yellow solid (1.05 g).

Preparation of 2-(5-trifluoromethyl-isoxazol-3-ylamino)-pyridine-3-carboxyaldehyde A mixture of 2-bromo-pyridine-3-carbaldehyde (280 mg), 5-trifluoromethyl-isoxazol-3-ylamine (152 mg), Pd(dba-3,5,3',5'-OMe)$_2$ (85 mg), Xantphos (58 mg) and caesium carbonate (455 mg) in toluene (3 ml) was heated at 150° C. in the microwave for 35 minutes. The reaction mixture was allowed to cool to room temperature, filtered, then evaporated under reduced pressure. The residue was purified by column chromatography (silica; ethyl acetate/hexane) to give the required product as a yellow solid (120 mg).

Stage 4

Preparation of ethyl 6-fluoro-2-oxo-1,2-dihydro[1,8]-naphthyridine-3-carboxylate A mixture of 2-amino-5-fluoropyridine-3-carboxaldehyde (2.80 g), diethyl malonate (6.40 g) and piperidine (0.85 g) in ethanol (50 ml) were heated to reflux with stirring for 18 hours, allowed to cool to ambient temperature then evaporated under reduced pressure. The residual solid obtained was washed with diethyl ether then filtered from solution, and sucked to dryness to give the required product as a pale brown solid, 3.97 g. $^1$H NMR (CDCl$_3$) δ: ca 11.0 (1H, bs), 9.33 (1H, m), 8.66 (1H, d), 8.42 (1H, s), 7.74 (1H, m), 4.45 (2H, q), 1.44 (3H, t).

The following compounds were prepared using a similar procedure:

From 2-amino-6-methylpyridine-3-carboxaldehyde, ethyl 7-methyl-2-oxo-1,2-dihydro[1,8]-naphthyridine-3-carboxylate, orange solid, m.p.153-156° C., $^1$H NMR (CDCl$_3$) δ: 8.46 (1H, s), 7.87 (1H, d), 7.10 (1H, d), 4.43 (2H, q), 2.68 (3H, s), 1.42 (3H, t). From 2-amino-5-fluoro-6-methylpyridine-3-carboxaldehyde, ethyl 6-fluoro-7-methyl-2-oxo-1,2-dihydro[1,8]-naphthyridine-3-carboxylate, orange-brown solid, $^1$H NMR (CDCl$_3$) δ: 8.40 (1H, s), 7.59 (1H, d), 4.43 (2H, q), 2.62 (3H, d), 1.42 (3H, t).

Stage 5

Preparation of ethyl 6-fluoro-1-methyl-2-oxo-1,2-dihydro[1,8]-naphthwidine-3-carboxylate To a stirred suspension of sodium hydride (0.11 g, 60% dispersion in mineral oil) in dry N,N-dimethylfonnamide (2 ml) at ambient temperature under an atmosphere of nitrogen was added a solution of ethyl 6-fluoro-2-oxo-1,2-dihydro[1,8]-naphthyridine-3-carboxylate (0.61 g) in dry N,N-dimethylformamide (20 ml) over 10 minutes. The mixture was stirred for 30 minutes then a solution of methyl iodide (0.55 g) in dry N,N-dimethylformamide (2 ml) was added over 5 minutes. The mixture was stirred for 2 hours then stored for 18 hours at ambient temperature. The dark orange solution was poured into water and extracted with ethyl acetate (three times). The extracts were combined, washed with water (three times), dried over magnesium sulfate, filtered and evaporated under reduced pressure. The residual solid was washed with isohexane then filtered from solution and sucked to dryness to give the required product as a paler yellow solid, 0.47 g. $^1$H NMR (CDCl$_3$) δ: 8.58 (1H, d), 8.28 (1H, s), 7.70 (1H, d), 4.45 (2H, q), 3.86 (3H, s), 1.42 (3H, t).

The following compounds were prepared using a similar procedure:

From ethyl 7-methyl-2-oxo-1,2-dihydro[1,8]-naphthyridine-3-carboxylate, ethyl 1,7-methyl-2-oxo-1,2-dihydro[1,8]-naphthyridine-3-carboxylate, yellow solid, $^1$H NMR (CDCl$_3$) δ: 8.34 (1H, s), 7.83 (1H, d), 7.10 (1H, d), 4.43 (2H, q), 3.86? (3H, s), 2.68 (3H, s), 1.42 (3H, t).

From ethyl 6-fluoro-7-methyl-2-oxo-1,2-dihydro[1,8]-naphthyridine-3-carboxylate, ethyl 6-fluoro-1,7-dimethyl-2-oxo-1,2-dihydro[1,8]-naphthyridine-3-carboxylate, orange solid, $^1$H NMR (CDCl$_3$) δ: 8.26 (1H, s), 7.57 (1H, d), 4.43 (2H, q), 3.84 (3H, s), 2.64 (3H, d), 1.42 (3H, t).

Stage 6

Preparation of 6-fluoro-1-methyl-2-oxo-1,2-dihydro[1,8]-naphthyridine-3-carboxylic acid To a stirred suspension of ethyl 6-fluoro-1-methyl-2-oxo-1,2-dihydro[1,8]-naphthyridine-3-carboxylate (0.46 g) in ethanol (15 ml) was added a solution of lithium hydroxide monohydrate (0.10 g) in water (5 ml) at ambient temperature. The mixture was stirred for 2 hours, evaporated under reduced pressure to a small volume, diluted with water then acidified with aqueous 2M hydrochloric acid. The solid formed was filtered from solution and sucked to dryness to give the required product as a colourless solid, 0.39 g. $^1$H NMR (CDCl$_3$+d6-DMSO) δ: 14.4 (1H, s), 8.92 (1H, s), 8.72 (1H, d), 7.94 (1H, m), 3.98 (3H, s).

The following compounds were prepared using a similar procedure from the corresponding carboxylic esters:

1,7-Methyl-2-oxo-1,2-dihydro[1,8]-naphthyridine-3-carboxylic acid, yellow solid, $^1$H NMR (CDCl$_3$+d6-DMSO) δ: 14.5 (1H, s), 8.88 (1H, s), 8.05 (1H, d), 7.27 (1H, d), 3.98 (3H, s), 2.74 (3H, s).

6-Fluoro-1,7-dimethyl-2-oxo-1,2-dihydro[1,8]-naphthyridine-3-carboxylic acid, orange solid, $^1$H NMR (CDCl$_3$) δ: 14.4 (1H, s), 8.84 (1H, s), 7.75 (1H, d), 3.98 (3H, s), 2.72 (3H, d).

Stage 7

To a stirred suspension of 6-fluoro-1-methyl-2-oxo-1,2-dihydro[1,8]-naphthyridine-3-carboxylic acid (0.38 g) in dry dichloromethane (20 ml) containing dry N,N-dimethylformamide (0.05 ml) was added oxalyl chloride (0.26 g). The mixture was stirred for 1.5 hours then evaporated under reduced pressure. The residue was suspended in dry acetonitrile (15 ml) with stirring and powdered 3 A molecular sieves were added followed by 1,3-cyclohexanedione (0.22 g) and dry triethylamine (0.24 ml). The mixture was stirred at ambient temperature for 2 hours then further dry triethylamine (0.47 ml) added followed by acetone cyanhydin (0.05 ml). The mixture was stirred for 18 hours, acidified with aqueous hydrochloric acid then extracted with ethyl acetate (three times). The extracts were combined, washed with water, dried over magnesium sulfate, filtered and evaporated under reduced pressure to a gum. The gum was purified by chromatography (silica; toluene/dioxane/triethylamine/ethanol/water, 100:40:20:20:5 by volume) to give, on acidification of the isolated triethylamino salt, the required product as a yellow, foamy solid (0.18 g). $^1$H NMR (CDCl$_3$) δ: 16.4 (1H, s), 8.50 (1H, d), 7.63 (1H, s), 7.62 (1H, m), 3.80 (3H, s), 2.78 (2H, t), 2.49 (2H, t), 2.08 (2H, m).

The following compounds were prepared using a similar procedure from the corresponding carboxylic acids:

2-(6-Fluoro-7-methyl-2-oxo-1,2-dihydro[1,8]-naphthyridine-3-carbonyl)-cyclohexane-1,3-dione, yellow solid, m.p.191-193° C., $^1$H NMR (CDCl$_3$) δ: 16.4 (1H, s), 7.62 (1H, s), 7.51 (1H, d), 3.80 (3H, s), 2.76 (2H, t), 2.63 (3H, s), 2.49 (2H, t), 2.07 (2H, m).

2-(1,7-Dimethyl-2-oxo-1,2-dihydro[1,8]-naphthyridine-3-carbonyl)-cyclohexane-1,3-dione, yellow solid, $^1$H NMR (CDCl$_3$) δ: 16.5 (1H, s), 7.78 (1H, d), 7.70 (1H, s), 7.04 (1H, d), 3.80 (3H, s), 2.75 (2H, t), 2.65 (3H, s), 2.49 (2H, t), 2.07 (2H, m).

Thus, according to the present invention there is further provided a method of making a compound of Formula (I) wherein Q=Q1 which comprises reacting together a compound of Formula (Ia')

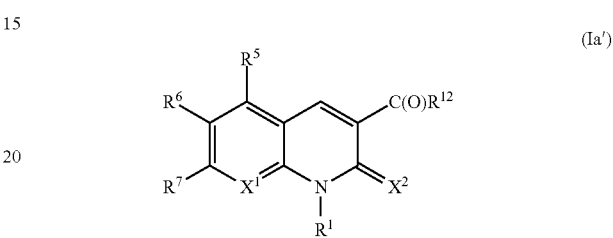

wherein the various substituents are as defined previously, and wherein $R^{12}$ is halogen or aryloxy with a compound of Formula (II)

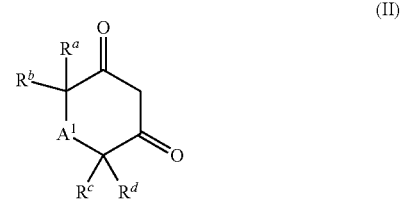

wherein the various substituents are as defined previously, in the presence of an inert organic solvent and a base. The method may further comprise a subsequent rearrangement step known to the skilled person using, for example, a suitable catalyst, for example acetone cyanhydrin.

Preferably $R^{12}$ is selected from the group consisting of fluorine, chlorine, bromine, and 4-nitrophenoxy. In an especially preferred embodiment $R^{12}$ is chlorine.

The present invention still further provides a compound of Formula (III)

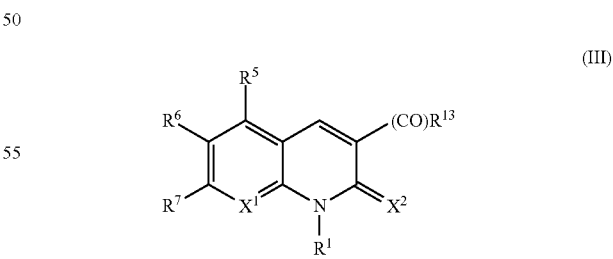

wherein
$R^1$, $R^5$, $R^6$, $R^7$, $X^1$, $X^2$ are as defined herein; and
$R^{13}$ is selected from the group consisting of halogen, $C_1$-$C_6$-alkoxy, OH, O$^-$M$^+$ wherein M$^+$ is an alkali metal cation or an ammonium cation with the exception of 1,6,7-Trimethyl-2-oxo-1,2-dihydro-quinoline-3-carboxylic acid, 1,6,7-Trimethyl-2-oxo-1,2-dihydro-quinoline-3-carboxylic acid methyl ester, 1,2-dihydro-2-oxo-1-[3-(trifluoromethyl)phenyl-1,8-naphthyridine-3-carboxylic acid and 1,2-dihydro-2-oxo-1-[3-(trifluoromethyl)phenyl-1,8-naphthyridine-3-carboxylic acid ethyl ester.

The present invention further provides the use of a compound of Formula (I) as a herbicide.

Examples of specific compounds of the present invention.

TABLE 1

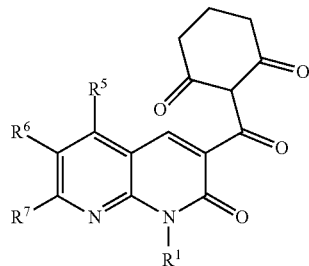

| Cmp | $R^1$ | $R^5$ | $R^6$ | $R^7$ | NMR |
|---|---|---|---|---|---|
| 1.1 | $CH_3$ | H | H | H | |
| 1.2 | $CH_3$ | H | H | $CH_3$ | |
| 1.3 | $CH_3$ | H | H | Et, | |
| 1.4 | $CH_3$ | H | H | n-Propyl | |
| 1.5 | $CH_3$ | H | H | i-Propyl | |
| 1.6 | $CH_3$ | H | H | c-Propyl | |
| 1.7 | $CH_3$ | H | H | n-Butyl | |
| 1.8 | $CH_3$ | H | H | i-Butyl | |
| 1.9 | $CH_3$ | H | H | s-Butyl | |
| 1.10 | $CH_3$ | H | H | c-Butyl | |
| 1.11 | $CH_3$ | H | H | $CH_2F$ | |
| 1.12 | $CH_3$ | H | H | $CF_2H$ | |
| 1.13 | $CH_3$ | H | H | $CF_3$ | |
| 1.14 | $CH_3$ | H | H | $C_2F_5$ | |
| 1.15 | $CH_3$ | H | H | $CH_2OCH_3$ | |
| 1.16 | $CH_3$ | H | H | O-cPentyl | |
| 1.17 | $CH_3$ | H | H | O—Ph | |
| 1.18 | $CH_3$ | H | H | $OCH(CH_3)CH_2CH_2CH_2CH_3$ | |
| 1.19 | $CH_3$ | H | F | $CH_3$ | |
| 1.20 | $CH_3$ | H | H | $SO_2Me$ | |
| 1.21 | $CH_3$ | H | H | OH | |
| 1.22 | $CH_3$ | H | H | $OCH(CH_3)_2$ | |
| 1.23 | $CH_3$ | H | H | $OCH_3$ | |
| 1.24 | $CH_3$ | H | H | $CF_3$ | |
| 1.25 | $CH_3$ | H | $CH_3$ | H | |
| 1.26 | $CH_3$ | H | H | $OC_2H_5$ | |
| 1.27 | $CH_3$ | H | H | Cl | |
| 1.28 | $CH_3$ | H | F | H | |
| 1.29 | $CH_3$ | H | H | H | 2.04-2.10(2H, m); 2.48-2.52(2H, t); 2.74-2.80(2H, t); 3.82(3H, s); 7.18-7.22(1H, m); 7.70(1H, s); 7.90-7.92(1H, dd); 8.63-8.65(1H, dd); 16.5(1H, s). |
| 1.30 | $CH_3$ | H | H | $OC_2H_5$ | |
| 1.31 | $CH_3$ | H | H | $OC_2H_5$ | |
| 1.32 | $CH_3$ | H | Cl | H | |
| 1.33 | $CH_3$ | H | H | H | |
| 1.34 | $CH_3$ | H | H | H | |
| 1.35 | $CH_3$ | H | H | $CHFCH_3$ | |
| 1.36 | $CH_3$ | H | H | $CF_2CH_3$ | |
| 1.37 | $CH_3$ | H | H | $CF(CH_3)_2$ | |
| 1.38 | $CH_3$ | H | F | $CHFCH_3$ | |
| 1.39 | $CH_3$ | H | F | $CF_2CH_3$ | |
| 1.40 | $CH_3$ | H | F | $CF(CH_3)_2$ | |
| 1.41 | $CH_3$ | H | F | $CH_3$ | |
| 1.42 | $CH_3$ | $CH_3$ | H | $CH_3$ | 2.05-2.11(2H, m); 2.48-2.52(2H, t); 2.53(3H, s); 2.59(3H, s); 2.72-2.76(2H, t); 3.80(3H, s); 6.99(1H, s); 7.94(1H, s); 16.5(1H, s). |
| 1.43 | methoxymethyl | H | F | H | 2.05-2.11(2H, m); 2.46-2.50(2H, t); 2.76-2.80(2H, t); 3.50(3H, s); 5.92(2H, s); 7.60-7.64(1H, m); 7.63(1H, s); 8.53-8.55(1H, d); 16.4(1H, s). |
| 1.44 | methoxyethyl | H | F | H | 2.04-2.12(2H, m); 2.46-2.50(2H, br t); 2.74-2.78(2H, br t); 3.36(3H, s); 3.68-3.72(2H, t); 4.72-4.76(2H, t); 7.60-7.64(1H, m); 7.64(1H, s); 8.50(1H, d); 16.4(1H, s). |

TABLE 1-continued

| Cmp | R¹ | R⁵ | R⁶ | R⁷ | NMR |
|---|---|---|---|---|---|
| 1.45 | 2,2 difluoroethyl | H | F | H | 2.04-2.12(2H, m); 2.42-2.52(2H, br s); 2.70-2.80(2H, br s); 4.90-4.98(2H, dt); 6.02-6.34(1H, tt); 7.64-7.68(2H, s & dd)); 8.49-8.50(1H, d); 16.3(1H, s). |
| 1.46 | methoxymethyl | H | F | $CH_3$ | 2.04-2.10(2H, m); 2.44-2.50(2H, br t); 2.63(3H, d); 2.72-2.78(2H, br t); 3.50(3H, s); 5.94(2H, s); 7.50-7.52(1H, d); 7.63(1H, s); 16.4(1H, s). |
| 1.47 | methoxyethyl | H | F | $CH_3$ | 1.98-2.04(2H, m); 2.38-2.42(2H, t); 2.54(3H, d); 2.66-2.70(2H, t); 3.32(3H, s); 3.61-3.65(2H, t); 4.65-4.69(2H, t); 7.43-7.45(1H, d); 7.55(1H, s); 16.3(1H, s). |
| 1.48 | 1,1-difluoro-but-1-enyl | H | F | H | 2.04-2.12(2H, m); 2.40-2.50(4H, m); 2.74-2.78(2H, t); 4.22-4.32(1H, 2 x t); 4.50-4.54(2H, t); 7.62-7.64(2H, m); 8.50(1H, d); 16.3(1H, s). |
| 1.49 | ethyl | H | F | H | 1.28-1.34(3H, t); 2.06-2.12(2H, m); 2.46-2.50(2H, t); 2.74-2.78(2H, t); 4.52-4.56(2H, q); 7.60-7.62(2H, m); 8.50-8.51(1H, d); 16.4(1H, s). |
| 1.50 | propyl | H | F | H | 0.98-1.02(3H, t); 1.70-1.78(2H, m); 2.06-2.12(2H, m); 2.46-2.52(2H, br s); 2.72-2.78(2H, br s); 4.40-4.46(2H, t); 7.60-7.64(2H, m); 8.49-8.50(1H, d); 16.4(1H, s). |
| 1.51 | i-Butyl | H | F | H | 0.92-0.94(6H, d); 2.06-2.12(2H, m); 2.26-2.34(1H, m); 2.46-2.50(2H, t); 2.74-2.78(2H, t); 4.44-4.46(1H, d); 7.58-7.62(2H, m); 8.48-8.49(1H, d); no enol H |
| 1.52 | 1-propenyl | H | F | H | 2.04-2.10(2H, m); 2.42-2.54(2H, br s); 2.70-2.80(2H, br s); 5.00-5.22(4H, m); 5.92-6.02(1H, m); 7.62-7.66(2H, m); 8.49-8.50(1H, d); 16.4(1H, s). |

TABLE 2

| Compound | R¹ | R⁵ | R⁶ | R⁷ |
|---|---|---|---|---|
| 2.1 | $CH_3$ | H | H | H |
| 2.2 | $CH_3$ | H | H | $CH_3$ |
| 2.3 | $CH_3$ | H | H | Et, |
| 2.4 | $CH_3$ | H | H | n-Propyl |
| 2.5 | $CH_3$ | H | H | i-Propyl |
| 2.6 | $CH_3$ | H | H | c-Propyl |
| 2.7 | $CH_3$ | H | H | n-Butyl |
| 2.8 | $CH_3$ | H | H | i-Butyl |
| 2.9 | $CH_3$ | H | H | s-Butyl |
| 2.10 | $CH_3$ | H | H | c-Butyl |
| 2.11 | $CH_3$ | H | H | $CH_2F$ |
| 2.12 | $CH_3$ | H | H | $CF_2H$ |
| 2.13 | $CH_3$ | H | H | $CF_3$ |
| 2.14 | $CH_3$ | H | H | $C_2F_5$ |
| 2.15 | $CH_3$ | H | H | $CH_2OCH_3$ |
| 2.16 | $CH_3$ | H | H | O-cPentyl |
| 2.17 | $CH_3$ | H | H | O—Ph |
| 2.18 | $CH_3$ | H | H | $OCH(CH_3)CH_2CH_2CH_3$ |
| 2.19 | $CH_3$ | H | F | $CH_3$ |
| 2.20 | $CH_3$ | H | H | $SO_2Me$ |
| 2.21 | $CH_3$ | H | H | OH |
| 2.22 | $CH_3$ | H | H | $OCH(CH_3)_2$ |
| 2.23 | $CH_3$ | H | H | $OCH_3$ |
| 2.24 | $CH_3$ | H | H | $CF_3$ |

TABLE 2-continued

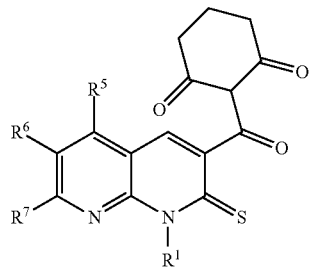

| Compound | R¹ | R⁵ | R⁶ | R⁷ |
|---|---|---|---|---|
| 2.25 | $CH_3$ | H | $CH_3$ | H |
| 2.26 | $CH_3$ | H | H | $OC_2H_5$ |
| 2.27 | $CH_3$ | H | H | Cl |
| 2.28 | $CH_3$ | H | F | H |
| 2.29 | $CH_3$ | H | H | H |
| 2.30 | $CH_3$ | H | H | $OC_2H_5$ |
| 2.31 | $CH_3$ | H | H | $OC_2H_5$ |
| 2.32 | $CH_3$ | H | Cl | H |
| 2.33 | $CH_3$ | H | H | H |

TABLE 2-continued

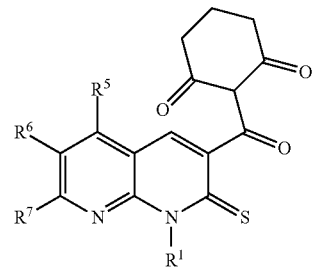

| Compound | R¹ | R⁵ | R⁶ | R⁷ |
|---|---|---|---|---|
| 2.34 | $CH_3$ | H | H | H |
| 2.35 | $CH_3$ | H | H | $CHFCH_3$ |
| 2.36 | $CH_3$ | H | H | $CF_2CH_3$ |
| 2.37 | $CH_3$ | H | H | $CF(CH_3)_2$ |
| 2.38 | $CH_3$ | H | F | $CHFCH_3$ |
| 2.39 | $CH_3$ | H | F | $CF_2CH_3$ |
| 2.40 | $CH_3$ | H | F | $CF(CH_3)_2$ |
| 2.41 | $CH_3$ | H | F | $CH_3$ |

TABLE 3

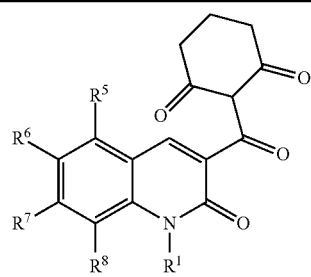

| Cmp | R¹ | R⁵ | R⁶ | R⁷ | R⁸ | NMR |
|---|---|---|---|---|---|---|
| 3.1 | $CH_3$ | H | H | H | $CH_3$ | |
| 3.2 | $CH_3$ | H | H | $CH_3$ | $CH_3$ | |
| 3.3 | $CH_3$ | H | H | Et, | $CH_3$ | |
| 3.4 | $CH_3$ | H | H | n-Propyl | $CH_3$ | |
| 3.5 | $CH_3$ | H | H | i-Propyl | $CH_3$ | |
| 3.6 | $CH_3$ | H | H | c-Propyl | $CH_3$ | |
| 3.7 | $CH_3$ | H | H | n-Butyl | $CH_3$ | |
| 3.8 | $CH_3$ | H | H | i-Butyl | $CH_3$ | |
| 3.9 | $CH_3$ | H | H | s-Butyl | $CH_3$ | |
| 3.10 | $CH_3$ | H | H | c-Butyl | $CH_3$ | |
| 3.11 | $CH_3$ | H | H | $CH_2F$ | $CH_3$ | |
| 3.12 | $CH_3$ | H | H | $CF_2H$ | $CH_3$ | |
| 3.13 | $CH_3$ | H | H | $CF_3$ | $CH_3$ | |
| 3.14 | $CH_3$ | H | H | $C_2F_5$ | $CH_3$ | |
| 3.15 | $CH_3$ | H | H | $CH_2OCH_3$ | $CH_3$ | |
| 3.16 | $CH_3$ | H | H | O-cPentyl | $CH_3$ | |
| 3.17 | $CH_3$ | H | H | O—Ph | $CH_3$ | |
| 3.18 | $CH_3$ | H | H | $OCH(CH_3)CH_2CH_2CH_2CH_3$ | $CH_3$ | |
| 3.19 | $CH_3$ | H | F | $CH_3$ | $CH_3$ | |
| 3.20 | $CH_3$ | H | H | $SO_2Me$ | $CH_3$ | |
| 3.21 | $CH_3$ | H | H | OH | $CH_3$ | |
| 3.22 | $CH_3$ | H | H | $OCH(CH_3)_2$ | $CH_3$ | |
| 3.23 | $CH_3$ | H | H | $OCH_3$ | $CH_3$ | |
| 3.24 | $CH_3$ | H | H | $CF_3$ | $CH_3$ | |
| 3.25 | $CH_3$ | H | $CH_3$ | H | $CH_3$ | |
| 3.26 | $CH_3$ | H | H | $OC_2H_5$ | $CH_3$ | |
| 3.27 | $CH_3$ | H | H | Cl | $CH_3$ | |
| 3.28 | $CH_3$ | H | F | H | $CH_3$ | |
| 3.29 | $CH_3$ | H | H | H | $CH_3$ | |
| 3.30 | $CH_3$ | H | H | $OC_2H_5$ | $CH_3$ | |
| 3.31 | $CH_3$ | H | H | $OC_2H_5$ | $CH_3$ | |
| 3.32 | $CH_3$ | H | Cl | H | $CH_3$ | |
| 3.33 | $CH_3$ | H | H | H | $CH_3$ | |
| 3.34 | $CH_3$ | H | H | H | $CH_3$ | |
| 3.35 | $CH_3$ | H | H | $CHFCH_3$ | $CH_3$ | |

TABLE 3-continued

| | | | | | | NMR |
|---|---|---|---|---|---|---|
| 3.36 | CH$_3$ | H | H | CF$_2$CH$_3$ | CH$_3$ | |
| 3.37 | CH$_3$ | H | H | CF(CH$_3$)$_2$ | CH$_3$ | |
| 3.38 | CH$_3$ | H | F | CHFCH$_3$ | CH$_3$ | |
| 3.39 | CH$_3$ | H | F | CF$_2$CH$_3$ | CH$_3$ | |
| 3.40 | CH$_3$ | H | F | CF(CH$_3$)$_2$ | CH$_3$ | |
| 3.41 | CH$_3$ | H | F | CH$_3$ | CH$_3$ | |
| 3.42 | CH$_3$ | H | H | Br | H | 2.04-2.10(2H, m); 2.46-2.50(2H, t); 2.72-2.76(2H, t); 3.67(3H, s); 7.34-7.38(1H, dd); 7.44-7.48(1H, d); 7.52(1H, s); 7.69(1H, s); 16.5(1H, s). |

TABLE 4

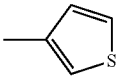

| Cmp | R$^1$ | R$^5$ | R$^6$ | R$^7$ | NMR |
|---|---|---|---|---|---|
| 4.1 | 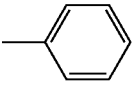 | H | H | H | |
| 4.2 | 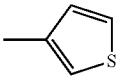 | H | H | H, | (1H, dd), 7.96 (1H, dd), 7.82 (1H, s), 7.56 (2H, t), 7.48 (1H, t), 7.32 (2H, d), 7.18 1H, dd). 2.70 (2H, bs), 2.46 (bs), 2.20 (2H, quintet) |
| 4.3 | 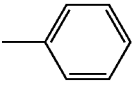 | H | F | H | 2.00-2.06(2H, m); 2.42-2.48(2H, br t); 2.70-2.74(2H, t); 7.05-7.07(1H, dd); 7.36-7.37(1H, d); 7.46-7.50(1H, m); 7.64-7.68(1H, dd); 7.70(1H, s); 8.39-8.40(1H, d); 16.3(1H, s). |
| 4.4 | 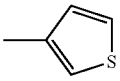 | H | F | H | 2.00-2.06(2H, m); 2.40-2.58(2H, br s); 2.58-2.78(2H, br t); 7.29-7.31(2H, d); 7.46-7.50(1H, m); 7.54-7.58(2H, m); 7.66-7.70(1H, dd); 7.74(1H, s); 8.34(1H, d); 16.3(1H, s). |
| 4.5 | 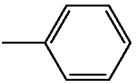 | H | F | CF$_3$ | |
| 4.6 | 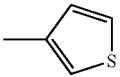 | H | F | CF$_3$ | |
| 4.7 | 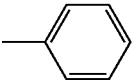 | H | H | CH$_3$ | |
| 4.8 | 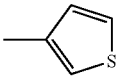 | H | H | CH$_3$ | |
| 4.9 | 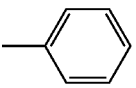 | H | F | CH$_3$ | 2.00-2.06(2H, m); 2.44-2.46(3H, d); 2.50-2.64(4H, br s); 7.04-7.06(1H, d); 7.34(1H, d); 7.40-7.44(1H, m); 7.53-7.55(1H, d); 7.70(1H, s); 16.3(1H, hump). |
| 4.10 | | H | F | CH$_3$ | 2.00-2.06(2H, m); 2.40-2.42(3H, d); 2.44-2.48(2H, br t); 2.70-2.74(2H, br t); 7.26-7.28(2H, d); 7.43-7.47(1H, m); 7.50-7.58(3H, m); 7.74(1H, s); 16.4(1H, s). |

TABLE 4-continued

| Cmp | R¹ | R⁵ | R⁶ | R⁷ | NMR |
|---|---|---|---|---|---|
| 4.11 | 3-CF₃-phenyl- | H | F | H | 2.00-2.08(2H, m); 2.40-2.50(2H, br s); 2.70-2.78(2H, br s); 7.50-7.54(1H, m); 7.58(1H, s); 7.64-7.74(4H, m); 8.30(1H, d); 16.3(1H, s). |
| 4.12 | (2,3-dihydro-1,4-benzodioxin-6-yl) | H | F | H | 2.00-2.06(2H, m); 2.40-2.55(2H, br s); 2.55-2.75(2H, br s); 4.30(4H, s); 6.74-6.78(1H, dd); 6.84(1H, s); 7.00-7.02(1H, d); 7.64-7.68(1H, dd); 7.72(1H, s); 8.39(1H, d); 16.3(1H, s). |
| 4.13 | (1,3-benzodioxol-5-yl) | H | F | H | 2.00-2.08(2H, m); 2.40-2.50(2H, br s); 2.68-2.76(2H, br s); 6.04-6.08(2H, d); 6.74-6.78(1H, d); 6.76(1H, s); 6.94-6.96(1H, d); 7.65-7.69(1H, dd); 7.72(1H, s); 8.39(1H, d); 16.3(1H, s). |
| 4.14 | -benzyl | H | F | H | 2.04-2.10(2H, m); 2.46-2.54(2H, br s); 2.72-2.80(2H, br s); 5.69(2H, s); 7.18-7.28(3H, m); 7.42-7.46(2H, d); 7.60-7.64(2H, m); 8.47-8.48(1H, d); 16.4(1H, s). |
| 4.15 | 2-fluorobenzyl | H | F | H | 2.02-2.10(2H, m); 2.44-2.48(2H, t); 2.72-2.76(2H, t); 5.76(2H, s); 6.96-7.08(3H, m); 7.14-7.20(1H, m); 7.62-7.66(1H, dd); 7.68(1H, s); 8.42-8.43(1H, d); 16.3(1H, s). |
| 4.16 | Phenoxyethyl- | H | F | H | 2.04-2.12(2H, m); 2.46-2.50(2H, t); 2.74-2.78(2H, t); 4.26-4.30(2H, t); 4.90-4.94(2H, t); 6.90-6.92(3H, m); 7.23-7.25(2H, d); 7.61-7.65(2H, m); 8.49-8.50(1H, d); 16.4(1H, s). |
| 4.17 | 4-methoxybenzyl | H | F | H | 2.04-2.12(2H, m); 2.48-2.52(2H, br t); 2.74-2.78(2H, t); 3.74(3H, s); 5.62(2H, s); 6.78-6.80(2H, d); 7.42-7.44(2H, d); 7.58-7.62(2H, m); 8.59-8.60(1H, d); 16.4(1H, s). |
| 4.18 | 4-methoxyphenyl | H | F | H | 2.00-2.06(2H, m); 2.42-2.48(2H, br t); 2.70-2.74(2H, t); 3.86(3H, s); 7.04-7.06(2H, m); 7.20-7.22(2H, m); 7.65-7.69(1H, dd); 7.73(1H, s); 8.37-8.38(1H, d); 16.3(1H, s). |
| 4.19 | 3-ethoxyphenyl | H | F | H | 1.38-1.42(3H, t); 2.00-2.08(2H, m); 2.42-2.46(2H, br t); 2.70-2.74(2H, t); 4.00-4.08(2H, br q); 6.80-7.24 (3H, m); 7.42-7.46(1H, t); 7.66-7.70(1H, dd); 7.74(1H, s); 8.36-8.37(1H, m); 16.3(1H, s). |
| 4.20 | 2-methoxy-pyridin-5-yl | H | F | H | 2.00-2.06(2H, m); 2.42-2.46(2H, br t); 2.71-2.75(2H, t); 4.00(3H, s); 6.90-6.92(1H, d); 7.50-7.54(1H, dd); 7.66-7.70(1H, dd); 7.74(1H, s); 8.12-8.13(1H, d); 8.34-8.35(1H, d); 16.3(1H, s). |
| 4.21 | phenyl | H | H | methoxy | 16.41 (1H, brs), 7.89 (1H, s), 7.82 (1H, d), 7.53-7.49 (2H, m), 7.44-7.40(1H, m), 7.31-7.28 (2H, m), 6.62 (1H, d), 3.55 (3H, s), 2.69 (2H, t), 2.47 (2H, t), 2.02 (2H, qn). |
| 4.22 | 2-methylphenyl | H | F | H | 16.22 (1H, s), 8.36 (1H, d), 7.78 (1H, 1), 7.68 (1H, dd), 7.33-7.42 (3H, m), 7.14 (1H, d), 2.71 (2H, t), 2.40-2.48 (2H, m), 2.09 (3H, s), 2.00-2.06 (2H, m) |
| 4.23 | 3,5-dichlorophenyl | H | F | H | 2.00-2.08(2H, m); 2.44-2.48(2H, br t); 2.72-2.76(2H, t); 7.24(2H, s); 7.47-7.48(1H, t); 7.66-7.70(1H, dd); 7.72(1H, s); 8.34-8.35(1H, d); 16.3(1H, s). |

TABLE 4-continued

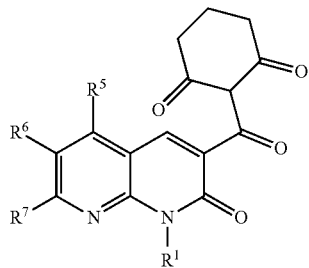

| Cmp | R¹ | R⁵ | R⁶ | R⁷ | NMR |
|---|---|---|---|---|---|
| 4.24 | 4-methylphenyl | H | F | H | 1.98-2.06(2H, br m); 2.42-2.46(5H, s + t); 2.70-2.74(2H, t); 7.16-7.18(2H, d); 7.34-7.36(2H, d); 7.65-7.69(1H, dd); 7.74(1H, s); 8.37-8.38(1H, d); 16.3(1H, s). |
| 4.25 | 3-chlorophenyl | H | F | H | 2.00-2.08(2H, m); 2.44-2.48(2H, br t); 2.72-2.76(2H, t); 7.20-7.22(1H, d); 7.32(1H, s); 7.44-7.50(2H, m); 7.66-7.70(1H, dd); 7.74(1H, s); 8.32-8.33(1H, d); 16.3(1H, s). |
| 4.26 | 2,4-dichlorophenyl | H | F | H | 16.22 (1H, s), 8.34 (1H, d), 7.78 (1H, 1), 7.71 (1H, dd), 7.62 (1H, d), 7.44 (1H, dd), 7.32 (1H, d), 2.70-2.75 (2H, m), 2.36-2.53 (2H, m), 2.09 (3H, s), 1.98-2.12 (2H, m) |
| 4.27 | 2-methyl-pyridin-6-yl | H | F | H | 8.30 (1H, d), 7.88 (1H, t), 7.77 (1H, t), 7.68 (1H, dd), 7.34 (1H, d), 7.24 (1H, d), 2.72 (2H, bs), 2.65 (3H, s), 2.45 (2H, bs), 2.00-2.06 (2H, m) |
| 4.28 | 2-chlorophenyl | H | F | H | 16.22 (1H, s), 8.34(1H, d), 7.78 (1H, 1), 7.68 (1H, dd), 7.56-4.62 (1H, m), 7.43-7.48 (2H, m), 7.36-7.40 (1H, m), 2.68-2.74 (2H, m), 2.35-2.45(2H, m), 2.09 (3H, s), 2.00-2.08 (2H, m) |
| 4.29 | 3,5-dimethylphenyl | H | F | H | 16.29(1H, s), 8.38(1H, d), 7.73(1H, s), 7.65(1H, dd), 7.10(1H, s), 6.90(2H, s), 2.71(2H, t), 2.45(2H, t), 2.37(6H, s), 2.03(2H, t) |
| 4.30 | 4-chlorophenyl | H | F | H | 16.29(1H, s), 8.34(1H, d), 7.74(1H, s), 7.68(1H, dd), 7.52(2H, d), 7.25(2H, d), 2.72(2H, t), 2.44(2H, br t), 2.03(2H, m) |
| 4.31 | 4-phenylphenyl | H | F | H | 16.33(1H, s), 8.38(1H, d), 7.76(3H, m), 7.70 (1H, dd), 7.64(2H, m), 7.46(2H, m), 7.37(3H, m), 2.72(2H, t), 2.46(2H, br t), 2.03(2H, m) |
| 4.32 | 3,4-dichlorophenyl | H | F | H | 16.28(1H, s), 8.34(1H, d), 7.73(1H, s), 7.68(1H, dd), 7.61(1H, d), 7.43(1H, d), 7.17(1H, m), 2.73(2H, t), 2.45(2H, br t), 2.04(2H, m) |
| 4.33 | 2-methoxyphenyl | H | F | H | 16.25(1H, s), 8.33(1H, d), 7.78(1H, s), 7.67 (1H, dd), 7.47(1H, td), 7.27(dd), 7.12(1H, td), 7.08(1H, dd) |
| 4.34 | 2-trifluoro-methylphenyl | H | F | H | 8.30(1H, d), 7.86(1H, d), 7.78(1H, s), 7.76 (1H, t), 7.68(1H, dd), 7.63(1H, t), 7.39(1H, d), 2.65-2.76(2H, m), 2.33-2.53(2H, m), 2.09(3H, s), 1.96-2.10(2H, m). |
| 4.35 | 2,4-difluorophenyl | H | F | H | 16.25(1H, s), 8.34(1H, d), 7.75(1H, s), 7.70 (1H, dd), 7.38-7.30(1H, m), 7.08-7.00(2H, m), 2.68-2.75(2H, m), 2.36-2.53(2H, m), 2.09(3H, s), 1.98-2.10(2H, m) |
| 4.36 | 2-nitrophenyl | H | F | H | 16.30(1H, s), 8.30-8.25(2H, m), 7.84-7.79(2H, m), 7.71-6.65(2H, m), 7.52(1H, dd), 2.70-2.75 (2H, m), 2.33-2.53(2H, m), 2.09(3H, s), 1.96-2.10(2H, m) |
| 4.37 | 2,5-dimethylphenyl | H | F | H | 16.10(1H, s), 8.36(1H, d), 7.83(1H, s), 7.72(1H, dd), 7.30(1H, t), 7.21(1H, s), 2.71 (2H, t), 2.42(2H, t), 2.10(2H, quintet) |

Biological Examples

Seeds of a variety of test species were sown in standard soil in pots (*Alopecurus myosuroides* (ALOMY), *Setaria faberi* (SETFA), *Echinochloa crus-galli* (ECHCG), *Abuthilon theophrasti* (ABUTH) and *Amaranthus retoflexus* (AMARE)). After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds were applied at 250 g/ha. The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

| | POST Application | | | | | PRE Application | | | | |
|---|---|---|---|---|---|---|---|---|---|---|
| Compound | ABUTH | AMARE | SETFA | ALOMY | ECHCG | ABUTH | AMARE | SETFA | ALOMY | ECHCG |
| 1.2 | 80 | 80 | 80 | 40 | 80 | 70 | 40 | 70 | 20 | 90 |
| 1.19 | 80 | 80 | 80 | 40 | 80 | 80 | 100 | 90 | 30 | 90 |
| 1.28 | 80 | 80 | 80 | 60 | 80 | 70 | 100 | 60 | 20 | 100 |
| 1.29 | 90 | 90 | 90 | 30 | 80 | 90 | 100 | 10 | 30 | 100 |
| 1.42 | 50 | 70 | 60 | 0 | 70 | 0 | 0 | 0 | 0 | 0 |
| 1.43 | 80 | 80 | 80 | 60 | 80 | 100 | 100 | 100 | 40 | 100 |
| 1.44 | 90 | 80 | 80 | 80 | 80 | 90 | 100 | 100 | 90 | 100 |
| 1.45 | 80 | 80 | 80 | 60 | 80 | 100 | 100 | 80 | 70 | 100 |
| 1.46 | 100 | 70 | 70 | 70 | 80 | 80 | 100 | 80 | 60 | 100 |
| 1.47 | 70 | 70 | 80 | 80 | 90 | 90 | 100 | 90 | 50 | 90 |
| 1.48 | 80 | 40 | 80 | 70 | 80 | 90 | 100 | 90 | 80 | 100 |
| 1.49 | 80 | 70 | 70 | 70 | 80 | 90 | 100 | 90 | 60 | 100 |
| 1.50 | 80 | 70 | 80 | 70 | 80 | 90 | 90 | 100 | 80 | 100 |
| 3.42 | 90 | 80 | 70 | 20 | 80 | 50 | 80 | 0 | 10 | 70 |
| 4.3 | 90 | 90 | 90 | 80 | 90 | 100 | 100 | 100 | 70 | 100 |
| 4.4 | 90 | 80 | 90 | 90 | 90 | 100 | 100 | 100 | 90 | 100 |
| 4.9 | 80 | 80 | 80 | 90 | 80 | 100 | 100 | 100 | 90 | 100 |
| 4.11 | 100 | 90 | 90 | 90 | 90 | 90 | 100 | 80 | 70 | 90 |
| 4.15 | 80 | 50 | 70 | 30 | 80 | 70 | 50 | 0 | 0 | 80 |
| 4.16 | 80 | 50 | 60 | 40 | 80 | 50 | 30 | 20 | 20 | 50 |
| 4.17 | 70 | 50 | 60 | 0 | 80 | 70 | 90 | 20 | 0 | 70 |
| 4.18 | 80 | 80 | 80 | 80 | 80 | 90 | 90 | 70 | 70 | 100 |
| 4.20 | 80 | 60 | 80 | 80 | 80 | 100 | 100 | 70 | 90 | 100 |
| 4.22 | 80 | 70 | 80 | 80 | 70 | 90 | 100 | 100 | 90 | 100 |
| 4.23 | 80 | 80 | 70 | 70 | 80 | 80 | 70 | 90 | 90 | 100 |
| 4.24 | 90 | 80 | 80 | 70 | 80 | 100 | 100 | 90 | 80 | 100 |
| 4.25 | 80 | 70 | 80 | 80 | 80 | 90 | 50 | 100 | 90 | 100 |
| 4.28 | 80 | 80 | 80 | 70 | 80 | 100 | 50 | 100 | 90 | 100 |
| 4.33 | 80 | 80 | 90 | 100 | 90 | 100 | 100 | 100 | 100 | 100 |
| 4.34 | 80 | 80 | 80 | 90 | 90 | 100 | 100 | 100 | 100 | 100 |
| 4.35 | 80 | 90 | 80 | 90 | 90 | 100 | 100 | 100 | 90 | 100 |
| 4.36 | 80 | 80 | 80 | 90 | 90 | 100 | 100 | 100 | 90 | 100 |

The invention claimed is:

1. A herbicidal compound of Formula (I):

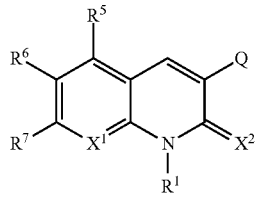

or an agronomically acceptable salt of said compound, wherein:—

$R^1$ is selected from the group consisting of hydrogen, $C_1$-$C_6$alkyl, $C_1$-$C_6$haloalkyl, $C_1$-$C_3$alkoxy-$C_1$-$C_3$ alkyl, $C_1$-$C_3$ alkoxy-$C_1$-$C_3$alkoxy-$C_1$-$C_3$-alkyl, $C_1$-$C_3$alkoxy-$C_1$-$C_3$-haloalkyl, $C_1$-$C_3$-alkoxy-$C_1$-$C_3$-alkoxy-$C_1$-$C_3$-haloalkyl, $C_4$-$C_6$-oxasubstituted cycloalkoxy-$C_1$-$C_3$-alkyl, $C_4$-$C_6$-oxasubstituted cycloalkyl-$C_1$-$C_3$-alkoxy-$C_1$-$C_3$-alkyl, $C_4$-$C_6$-oxasubstituted cycloalkoxy-$C_1$-$C_3$-haloalkyl, $C_4$-$C_6$-oxasubstituted cycloalkyl-$C_1$-$C_3$-alkoxy-$C_1$-$C_3$-haloalkyl, ($C_1$-$C_3$ alkanesulfonyl-$C_1$-$C_3$ alkylamino)-$C_1$-$C_3$ alkyl, ($C_1$-$C_3$ alkanesulfonyl-$C_3$-$C_4$ cycloalkylamino)-$C_1$-$C_3$alkyl, $C_1$-$C_6$alkylcarbonyl-$C_1$-$C_3$alkyl, $C_3$-$C_6$cycloalkyl-$C_2$-$C_6$alkenyl, $C_3$-$C_6$alkynyl, $C_2$-$C_6$-alkenyl, $C_2$-$C_6$-haloalkenyl, cyano-$C_1$-$C_6$alkyl, arylcarbonyl-$C_1$-$C_3$alkyl, aryloxycarbonyl-$C_1$-$C_3$alkyl (wherein in both cases the aryl may be optionally substituted with one or more substituents from the group consisting of halo, $C_1$-$C_3$alkoxy, $C_1$-$C_3$alkyl, $C_1$-$C_3$haloalkyl), aryl-$C_1$-$C_6$alkyl (wherein the aryl may be optionally substituted with one or more substituents from the group consisting of halo, $C_1$-$C_3$-alkoxy, $C_1$-$C_3$-alkyl, $C_1$-$C_3$ haloalkyl) and a three- to ten-membered mono- or bicyclic ring system, which may be aromatic, saturated or partially saturated and can contain from 1 to 4 heteroatoms each independently selected from the group consisting of nitrogen, oxygen and sulphur the ring system being optionally substituted by one or more substituents selected from the group consisting of $C_1$-$C_3$alkyl, $C_1$-$C_3$haloalkyl, $C_1$-$C_3$alkenyl, $C_1$-$C_3$alkynyl, $C_1$-$C_3$ alkoxy, $C_1$-$C_3$ haloalkoxy, $C_1$-$C_6$alkyl-S(O)p—, $C_1$-$C_6$haloalkyl-S(O)p—, aryl, aryl-S(O)p, heteroaryl-S(O)p, aryloxy, heteroaryloxy, $C_1$-$C_3$ alkoxycarbonyl, $C_1$-$C_3$ alkylamino-S(O)p—, $C_1$-$C_3$ alkylamino-S(O)p-$C_1$-$C_3$ alkyl, $C_1$-$C_3$ dialkylamino-S(O)p—, $C_1$-$C_3$ dialkylamino-S(O)p-$C_1$-$C_3$ alkyl, $C_1$-$C_3$ alkylaminocarbonyl-, $C_1$-$C_3$ alkylaminocarbonyl-$C_1$-$C_3$ alkyl, $C_1$-$C_3$ dialkylaminocarbonyl, $C_1$-$C_3$ dialkylaminocarbonyl-$C_1$-$C_3$ alkyl, $C_1$-$C_3$ alkylcarbonylamino, $C_1$-$C_3$ alkyl-S(O)p-amino, cyano and nitro; the heteroaryl substituents containing one to three heteroatoms each independently selected from the group consisting of oxygen, nitrogen and sulphur, and wherein the aryl or heteroaryl component may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, phenyl, cyano and nitro;

$R^5$ is selected from the group consisting of hydrogen, chloro, fluoro and methyl;

$R^6$ is selected from the group consisting of hydrogen, fluorine, chlorine, hydroxyl and methyl;

$R^7$ is selected from the group consisting of hydrogen, cyano, nitro, halogen, hydroxyl, sulfhydryl, $C_1$-$C_6$alkyl, C$_3$-C$_6$cycloalkyl, C$_1$-C$_6$haloalkyl, C$_2$-C$_6$haloalkenyl, C$_2$-C$_6$alkenyl, aryl-C$_2$-C$_6$alkenyl, C$_3$-C$_6$alkynyl, C$_1$-C$_6$alkoxy, C$_4$-C$_7$cycloalkoxy, C$_1$-C$_6$haloalkoxy, C$_1$-C$_6$alkyl-S(O)p, C$_{3-6}$cycloalkyl-S(O)p, C$_1$-C$_6$haloalkyl-S(O)p, C$_3$-C$_6$ halocycloalkyl-S(O)p, C$_1$-C$_6$alkylcarbonylamino, (C$_1$-C$_6$alkylcarbonyl)C$_1$-C$_3$alkylamino, (C$_3$-C$_6$cycloalkylcarbonyl)amino, (C$_3$-C$_6$cycloalkylcarbonyl)C$_1$-C$_3$alkylamino, arylcarbonylamino, (arylcarbonyl)-C$_{1-3}$alkylamino, (heteroarylcarbonyl)amino, (heteroarylcarbonyl)C$_1$-C$_3$alkylamino, amino, C$_1$-C$_6$alkylamino, C$_2$-C$_6$dialkylamino, C$_2$-C$_6$alkenylamino, C$_1$-C$_6$alkoxy-C$_2$-C$_6$-alkylamino, (C$_1$-C$_6$alkoxy-C$_2$-C$_4$-alkyl)-C$_1$-C$_6$-alkylamino, C$_3$-C$_6$ cycloalkylamino, C$_3$-C$_6$ cyclohaloalkylamino, C$_1$-C$_3$alkoxy-C$_3$-C$_6$ cycloalkylamino, C$_3$-C$_6$ alkynylamino, dialkylamino in which the substituents join to form a 4-6 membered ring optionally containing oxygen and/or optionally substituted by C$_1$-C$_3$-alkoxy and/or halogen (especially fluorine), C$_2$-C$_6$dialkylaminosulfonyl, C$_1$-C$_6$alkylaminosulfonyl, C$_1$-C$_6$alkoxy-C$_1$-C$_6$alkyl, C$_1$-C$_6$alkoxy-C$_2$-C$_6$alkoxy, C$_1$-C$_6$alkoxy-C$_2$-C$_6$ alkoxy-C$_1$-C$_6$-alkyl, C$_3$-C$_6$alkenyl-C$_2$-C$_6$alkoxy, C$_3$-C$_6$alkynyl-C$_1$-C$_6$alkoxy, C$_1$-C$_6$alkoxycarbonyl, C$_1$-C$_6$alkylcarbonyl, C$_1$-C$_4$alkylenyl-S(O)p—R', C$_1$-C$_4$alkylenyl-CO$_2$—R', C$_1$-C$_4$alkylenyl-(CO)N—R'R', aryl, aryl-C$_1$-C$_3$alkyl, aryl-S(O)p, heteroaryl-S(O)p, aryloxy, a 5 or 6-membered heteroaryl, heteroaryl C$_1$-C$_3$ alkyl and heteroaryloxy, the heteroaryl containing one to three heteroatoms, each independently selected from the group consisting of oxygen, nitrogen and sulphur, wherein the aryl or heteroaryl component may be optionally substituted by one or more substituents selected from the group consisting of C$_1$-C$_3$alkyl, C$_1$-C$_3$haloalkyl, C$_1$-C$_3$ alkoxy, C$_1$-C$_3$haloalkoxy, halo, cyano and nitro;

X$^1$=N—(O)$_n$ or C—R$^8$;

X$^2$=O or S;

n=0 or 1;

p=0, 1 or 2;

R' is independently selected from the group consisting of hydrogen and C$_1$-C$_6$alkyl;

R$^8$ is selected from the group consisting of hydrogen, halogen, C$_1$-C$_6$alkyl, C$_1$-C$_6$haloalkyl, C$_1$-C$_6$alkylcarbonyl-C$_1$-C$_3$alkyl, C$_3$-C$_6$cycloalkyl-C$_2$-C$_6$alkenyl for example cyclohexylmethylenyl, C$_3$-C$_6$alkynyl, C$_2$-C$_6$-alkenyl, C$_1$-C$_6$alkoxy C$_1$-C$_6$alkyl, cyano-C$_1$-C$_6$-alkyl, arylcarbonyl-C$_1$-C$_3$-alkyl (wherein the aryl may be optionally substituted with one or more substituents selected from the group consisting of halo, C$_1$-C$_3$-alkoxy, C$_1$-C$_3$-alkyl, C$_1$-C$_3$ haloalkyl), aryl-C$_1$-C$_6$alkyl (wherein the aryl may be optionally substituted with one or more substituents from the group consisting of halo, C$_1$-C$_3$-alkoxy, C$_1$-C$_3$-alkyl, C$_1$-C$_3$ haloalkyl), C$_1$-C$_6$alkoxy C$_1$-C$_6$alkoxy C$_1$-C$_6$alkyl, aryl, 5 or 6-membered heteroaryl, a 5 or 6-membered heteroaryl-C$_1$-C$_3$-alkyl and heterocyclyl-C$_1$-C$_3$-alkyl, the heteroaryl or heterocyclyl containing one to three heteroatoms each independently selected from the group consisting of oxygen, nitrogen and sulphur, and wherein the aryl, heterocyclyl or heteroaryl component may be optionally substituted by one or more substituents from the group consisting of halogen, C$_1$-C$_3$alkyl, C$_1$-C$_3$haloalkyl and C$_1$-C$_3$ alkoxy, cyano and nitro;

Q is selected from the group consisting of:—

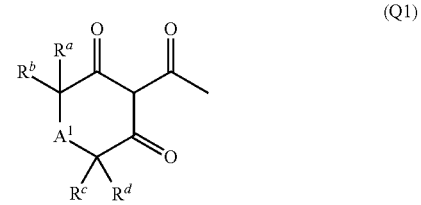
(Q1)

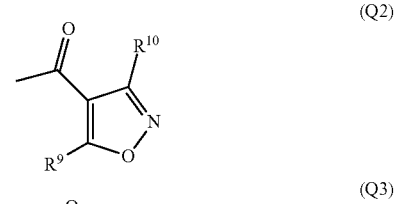
(Q2)

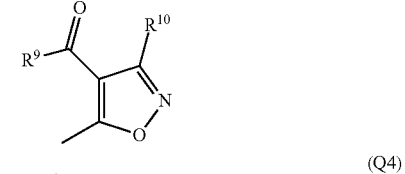
(Q3)

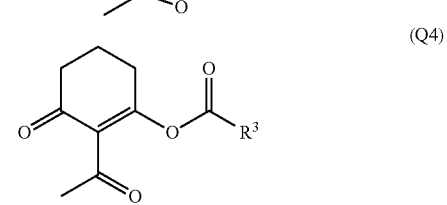
(Q4)

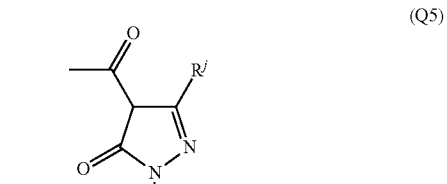
(Q5)

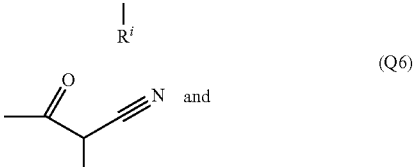
(Q6)

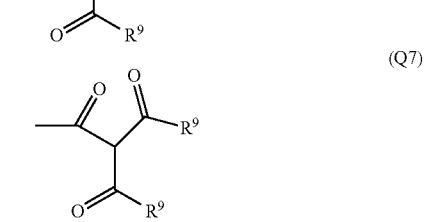
(Q7)

wherein

A$^1$ is selected from the group consisting of O, C(O), S, SO, SO$_2$ and (CR$^e$R$^f$)$_q$;

q=0, 1 or 2;

R$^a$, R$^b$, R$^c$, R$^d$, R$^e$ and R$^f$ are each independently selected from the group consisting of C$_1$-C$_4$alkyl which may be mono-, di- or tri-substituted by substituents selected from the group consisting of C$_1$-C$_4$alkoxy, halogen, hydroxy, cyano, hydroxycarbonyl, C$_1$-C$_4$alkoxycarbonyl, C$_1$-C$_4$alkylthio, C$_1$-C$_4$alkylsulfinyl, C$_1$-C$_4$alkylsulfonyl, C$_1$-C$_4$alkylcarbonyl, phenyl and heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkyl sulfonyl and $C_1$-$C_4$haloalkyl, the substituents on the nitrogen in the heterocyclic ring being other than halogen; or $R^a$, $R^b$, $R^c$, $R^d$, $R^e$ and $R^f$ are each independently selected from the group consisting of hydrogen, $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, the substituents on the nitrogen in the heterocyclic ring being other than halogen; or $R^a$ and $R^b$ together form a 3- to 5-membered carbocyclic ring which may be substituted by $C_1$-$C_4$alkyl and may be interrupted by oxygen, sulfur, S(O), $SO_2$, OC(O), $NR^g$ or by C(O); or $R^a$ and $R^c$ together form a $C_1$-$C_3$alkylene chain which may be interrupted by oxygen, sulfur, SO, $SO_2$, OC(O), $NR^h$ or by C(O); it being possible for that $C_1$-$C_3$alkylene chain in turn to be substituted by $C_1$-$C_4$alkyl;

$R^g$ and $R^h$ are each independently of the other $C_1$-$C_4$alkyl, $C_1$-$C_4$haloalkyl, $C_1$-$C_4$alkylsulfonyl, $C_1$-$C_4$alkylcarbonyl or $C_1$-$C_4$alkoxycarbonyl;

$R^i$ is $C_1$-$C_4$alkyl;

$R^j$ is selected from the group consisting of hydrogen, $C_1$-$C_4$ alkyl and $C_3$-$C_6$ cycloalkyl;

$R^3$ is selected from the group consisting of $C_1$-$C_6$alkyl, optionally substituted with halogen and/or $C_1$-$C_3$alkoxy, and $C_3$-$C_6$ cycloalkyl optionally substituted with halogen and/or $C_1$-$C_3$alkoxy;

$R^9$ is selected from the group consisting of cyclopropyl, $CF_3$ and i.-Pr;

$R^{10}$ is selected from the group consisting of hydrogen, I, Br, $SR^{11}$, $S(O)R^{11}$, $S(O)_2R^{11}$ and $CO_2R^{11}$; and $R^{11}$ is $C_{1-4}$ alkyl.

2. A herbicidal compound according to claim 1, wherein the three- to ten-membered mono- or bicyclic ring system of $R^1$ is selected from the group consisting of aryl, a 5 or 6-membered heteroaryl, a 5 or 6-membered heteroaryl-$C_1$-$C_3$alkyl and heterocyclyl-$C_1$-$C_3$alkyl, the heteroaryl or heterocyclyl containing one to three heteroatoms each independently selected from the group consisting of oxygen, nitrogen and sulphur, and wherein the aryl, heterocyclyl or heteroaryl component may be optionally substituted by one or more substituents selected from the group consisting of halo, $C_1$-$C_3$alkyl, $C_1$-$C_3$haloalkyl, $C_1$-$C_3$ alkoxy, cyano and nitro.

3. A herbicidal compound according to claim 1 or claim 2 having Formula (Ia)

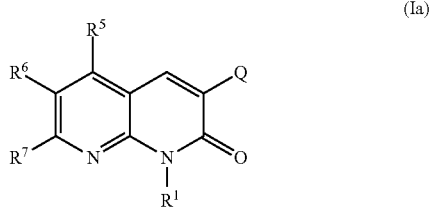

wherein $R^7$ is selected from the group consisting of hydrogen, hydroxyl, halogen, $C_1$-$C_6$alkyl, $C_3$-$C_6$cycloalkyl, $C_1$-$C_6$ haloalkyl, $C_1$-$C_6$ alkoxy, $C_1$-$C_6$ alkoxy-$C_2$-$C_6$-alkoxy, $C_1$-$C_6$-alkoxy-$C_1$-$C_6$ alkyl, $C_1$-$C_6$-alkoxy-$C_2$-$C_6$-alkoxy-$C_1$-$C_6$ alkyl, $C_1$-$C_6$alkylamino, $C_1$-$C_6$dialkylamino, $C_2$-$C_6$alkenylamino, $C_1$-$C_6$alkoxy-$C_2$-$C_3$-alkylamino, ($C_1$-$C_6$alkoxy-$C_2$-$C_4$-alkyl)-$C_1$-$C_6$-alkylamino, $C_3$-$C_6$ cycloalkylamino, $C_3$-$C_6$ cyclohaloalkylamino, $C_1$-$C_3$alkoxy-$C_3$-$C_6$ cycloalkylamino, $C_3$-$C_6$ alkynylamino and dialkylamino group in which the substituents join to form a 4-6 membered ring, optionally containing oxygen, and/or optionally substituted by $C_1$-$C_3$-alkoxy and/or halogen.

4. A herbicidal compound according to claim 3, wherein $R^7$ is selected from the group consisting of hydrogen, chloro, methyl, ethyl, 1-methylethyl, cyclopropyl, fluoromethyl, 1-fluoroethyl, 1,1-difluoroethyl, 2,2-difluoroethyl, 1-fluoro-1-methylethyl, 2,2,2-trifluoroethyl, difluorochloromethyl, methoxy, ethoxy, methoxymethyl, 1-methoxyethyl, 2-methoxyethoxy, 2-methoxyethoxymethyl, (2-methoxyethyl)amino and (2-methoxyethyl)methylamino.

5. A herbicidal compound according to claim 1 having Formula (Ib)

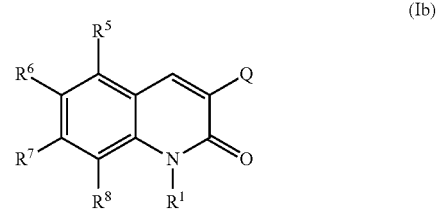

wherein $R^7$ is selected from the group consisting of hydrogen, cyano, halogen, nitro, $C_1$-$C_6$ haloalkyl, $C_1$-$C_3$ alkoxy$C_1$-$C_3$ haloalkyl, $C_1$-$C_3$ alkoxy$C_2$-$C_6$-alkoxy$C_1$-$C_3$ haloalkyl, $C_1$-$C_6$haloalkoxy, $C_1$-$C_6$alkylS(O)p, $C_{3-6}$cycloalkylS(O)p, $C_1$-$C_6$haloalkyl-S(O)p, $C_3$-$C_6$halocycloalkyl-S(O)p, aryl-S(O)p and heteroaryl-S(O)p.

6. A herbicidal compound according to claim 5, wherein $R^7$ is selected from the group consisting of chloro, fluoro, cyano, nitro, fluoromethyl, difluoromethyl, trifluoromethyl, 1-fluoroethyl, 1,1-difluoroethyl, 1-fluoro-1-methylethyl, difluorochloromethyl, difluoromethoxy, trifluoromethoxy, 1,1-difluoroethoxy, methylsulfinyl, methylsulfonyl, ethylsulfinyl, ethylsulfonyl, phenyl sulfinyl and phenyl sulfonyl.

7. A herbicidal compound according to claim 1, wherein Q is Q1.

8. A herbicidal compound according to claim 7, wherein $A^1$ is $CR^eR^f$ and wherein $R^a$, $R^b$, $R^c$, $R^d$, $R^e$ and $R^f$ are hydrogen and wherein q=1.

9. A herbicidal compound of claim 1, wherein $R^1$ is selected from the group consisting of hydrogen, $C_1$-$C_6$alkyl, $C_1$-$C_3$alkoxy$C_1$-$C_3$alkyl, $C_1$-$C_3$alkoxy $C_2$-$C_3$alkoxy$C_1$-$C_3$alkyl, $C_1$-$C_6$haloalkyl, $C_1$-$C_3$alkoxy-$C_1$-$C_3$haloalkyl, aryl (especially phenyl) and a 5 or 6-membered heteroaryl containing one to three heteroatoms each independently selected from the group consisting of oxygen, nitrogen and sulphur, and wherein the aryl or heteroaryl may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)p—, $C_1$-$C_6$haloalkyl-S(O)p—, cyano and nitro.

10. A herbicidal compound according to claim 9, wherein $R^1$ is selected from the group consisting of methyl, propyl, iso-butyl, methoxymethyl, methoxyethyl, 2,2 difluoroethyl, 1,1-difluoro-but-1-enyl, 1-propenyl, thiophenyl, benzyl, phenyl and phenoxy.

11. A herbicidal compound according to claim 1, wherein $R^6$ is hydrogen or fluorine.

12. An agronomically acceptable salt of the compound according claim 1, wherein the salt is selected from the group consisting of $Na^+$, $Mg^{2+}$ and $Ca^{2+}$.

13. A herbicidal composition comprising a herbicidal compound according to claim 1 and an agriculturally acceptable formulation adjuvant.

14. A herbicidal composition according to claim 13, further comprising at least one additional pesticide.

15. A herbicidal composition according to claim 14, wherein the additional pesticide is a herbicide or herbicide safener.

16. A method of selectively controlling weeds at a locus comprising crop plants and weeds, wherein the method comprises application to the locus of a weed controlling amount of a composition according to claim 1.

17. A method of making a compound of Formula (I) wherein Q=Q1 which comprises reacting together a compound of Formula (Ia')

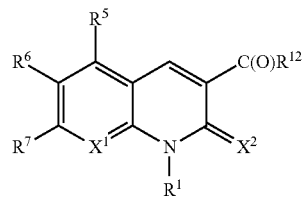

wherein the various substituents are as defined in claim 1, and wherein $R^{12}$ is halogen or aryloxy with a compound of Formula (II)

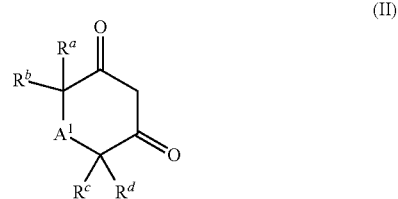

wherein the various substituents are as defined in claim 1, in the presence of an inert organic solvent and a base.

18. A compound of Formula (III)

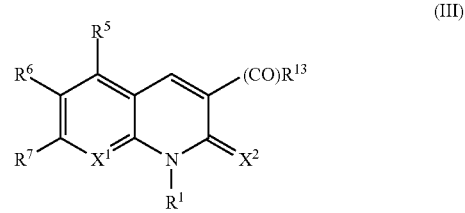

wherein
$R^1$, $R^5$, $R^6$, $R^7$, $X^1$, $X^2$ are as defined in claim 1 above; and
$R^{13}$ is selected from the group consisting of halogen, $C_1$-$C_6$-alkoxy, OH, $O^-M^+$ wherein $M^+$ is an alkali metal cation or an ammonium cation with the exception of 1,6,7-Trimethyl-2-oxo-1,2-dihydro-quinoline-3-carboxylic acid, 1,6,7-Trimethyl-2-oxo-1,2-dihydro-quinoline-3-carboxylic acid methyl ester, 1,2-dihydro-2-oxo-1-[3-(trifluoromethyl)phenyl-1,8-naphthyridine-3-carboxylic acid and 1,2-dihydro-2-oxo-1-[3-(trifluoromethyl)phenyl-1,8-naphthyridine-3-carboxylic acid ethyl ester.

* * * * *